United States Patent
Michaeli et al.

(10) Patent No.: US 6,548,066 B1
(45) Date of Patent: Apr. 15, 2003

(54) IMMUNOGENIC COMPOSITIONS TO THE CCK-B/GASTRIN RECEPTOR AND METHODS FOR THE TREATMENT OF TUMORS

(75) Inventors: Dov Michaeli, Larkspur, CA (US); Martyn Caplin, London (GB); Susan A. Watson, Nottingham (GB); Stephen Grimes, Davis, CA (US)

(73) Assignee: Aphton Corporation, Woodland, CA (US)

(*) Notice: Subject to any disclaimer, the term of this patent is extended or adjusted under 35 U.S.C. 154(b) by 0 days.

(21) Appl. No.: 09/076,372

(22) Filed: May 12, 1998

Related U.S. Application Data

(60) Provisional application No. 60/046,201, filed on May 12, 1997.

(51) Int. Cl.⁷ ............... A61K 39/385; A61K 38/10; C07K 17/06

(52) U.S. Cl. ............... 424/185.1; 424/184.1; 424/193.1; 424/198.1; 424/195.11; 530/326; 530/345; 530/402; 530/403; 530/388.22; 530/387.9; 530/391.1; 530/389.7; 514/2; 514/13

(58) Field of Search .......... 424/185.1, 195.11, 424/194.1, 193.1, 192.1, 155.1, 154.1, 197.1, 198.11, 198.1; 514/2, 13; 530/388.22, 387.9, 391.1, 389.7, 326, 345, 402, 403

(56) References Cited

U.S. PATENT DOCUMENTS

| | | | |
|---|---|---|---|
| 4,713,366 A | * 12/1987 | Stevens | |
| 4,840,939 A | 6/1989 | Leveen et al. | 514/25 |
| 4,925,922 A | 5/1990 | Byers et al. | |
| 4,971,792 A | 11/1990 | Steplewski et al. | 424/85.91 |
| 5,023,077 A | 6/1991 | Gevas | |
| 5,055,404 A | 10/1991 | Ueda et al. | |
| 5,162,504 A | 11/1992 | Horoszewisz | 530/388.2 |
| 5,242,799 A | 9/1993 | Samuel et al. | |
| 5,319,073 A | 6/1994 | Wank | 530/412 |
| 5,468,494 A | 11/1995 | Gevas | |
| 5,484,596 A | 1/1996 | Hanna, Jr. et al. | |
| 5,585,474 A | 12/1996 | Iwaki et al. | |
| 5,607,676 A | 3/1997 | Gevas | |
| 5,609,870 A | 3/1997 | Gevas | |
| 5,622,702 A | 4/1997 | Gevas | |
| 5,639,613 A | 6/1997 | Shay et al. | |
| 5,665,864 A | 9/1997 | Quaranta et al. | |
| 5,665,874 A | 9/1997 | Kuhajda et al. | |
| 5,688,506 A | 11/1997 | Grimes | |
| 5,703,213 A | 12/1997 | Wands et al. | |
| 5,723,718 A | 3/1998 | Berens | 800/2 |
| 5,750,119 A | 5/1998 | Srivastava | |
| 5,759,791 A | 6/1998 | Kuhajda et al. | |
| 5,785,970 A | 7/1998 | Gevas | |
| 5,827,691 A | 10/1998 | Iwaki et al. | 435/69.1 |
| 5,869,045 A | 2/1999 | Hellstrom et al. | 424/130.1 |
| 5,879,898 A | 3/1999 | Tarin et al. | |

FOREIGN PATENT DOCUMENTS

| | | |
|---|---|---|
| WO | 9008774 | 8/1990 |
| WO | 9400590 | 1/1994 |
| WO | 9513297 | 5/1995 |
| WO | 9851337 | 11/1998 |

OTHER PUBLICATIONS

Current Protocols in Molecular Biology, F.M. Ausubel, ed., John Wiley & Sons, New York, pp. 11.15.1–11.15.4, 1990.*
B.T. Brett et al., Abstract Gut 1998; 42(Suppl.), pp A26.
Kay Savage et al., Abstract Gut Apr. 1999 Supplement No. 1 vol. 44, pp A48.
Martyn Caplin, et al. "Expression and Processing of Gastrin" Journal of Hepatology, vol. 30 No. 3, Mar. 1999.
Susan Watson, et al. "Inhibitory Effects of the Gastrin Receptor" Cancer vol. 68; No. 6, Sep. 15, 1991, pp 1255–1260.
D.F. McWilliams et al. "Coexpression of Gastrin and Gastrin Receptors" Gut 1998; 42:795–798.
A. Smith, et al. Abstract Society for Neuroscience, vol. 21, No. 1–3, p. 189, 1995.
Susan Watson, et al. "Gastrimmune Raises Antibodies that Neutralize" Cancer Research vol. 56; No. 4 Feb. 15, 1996, pp 880–885.
Susan Watson, et al. Abstract Proceedings of the American Assoc. for Cancer Research vol. 38, Mar. 1997.
Susan Watson, et al. "Gastrin: growth enhancing effects on human gastric and colonic tumour cells" British Journal of Cancer (1989) 59. 554–558.
A.M. Smith et al. "Gastric carcinoid expresses the gastrin autocrine pathway" British Journal of Surgery 1998, 85, 1285–1289.
Susan Watson, et al., "Expression of CCKB/Gastrin Receptor Isoforms" Int. J. Cancer: Vol. 77, No. 4 (Aug. 1998).
Susan Watson et al., "A Comparison of an Anti–Gastrin Antibody" Int. J. Cancer: vol. 81, No. 2 (Apr. 1999).
M.E. Caplin, Abstract Gastroenterology vol. 114, No. 4, Part 2, Apr. 1998.

(List continued on next page.)

Primary Examiner—Anthony C. Caputa
Assistant Examiner—Anne L. Holleran
(74) Attorney, Agent, or Firm—White & Case LLP

(57) ABSTRACT

The invention concerns immunogens, immunogenic compositions and method for the treatment of gastrin-dependent tumors. The immunogens comprise a peptide from the CCK-B/gastrin-receptor conjugated to a spacer and to an immunogenic carrier. The immunogens are capable of inducing antibodies in vivo which bind to the CCK-B/gastrin-receptor in tumor cells, thereby preventing growth stimulating peptide hormones from binding to the receptors, and inhibiting tumor cell growth. The immunogens also comprise antibodies against the CCK-B/gastrin-receptor for passive immunization. The invention also concerns diagnostic methods for detecting gastrin-dependent tumors in vivo or from a tissue biopsy using the antibodies of the invention.

9 Claims, 16 Drawing Sheets

OTHER PUBLICATIONS

B.T. Brett et al. Abstract Gastroenterology vol. 114, No. 4, Part 2, Apr. 1998.

Susan Watson, et al. Abstract Gastroenterology vol. 114, No. 4, Part 2, Apr. 1998.

M.E. Caplin et al., Abstract Gastroenterology vol. 110, No. 4, Apr. 1996 (Suppl.).

S. Zeng et al., Abstract Gastroenterology vol. 110, No. 4, Apr. 1996 (Suppl.).

R.J.C. Steele et al., Abstract Gastroenterology vol. 108, No. 4, Apr. 1996 (Suppl.).

Houghton et al. Relative importance of position . . . In *Vaccine* 86 (Brown et al. eds).

Bystryn. Tumor vaccines. *Cancer and Metastasis Reviews* 9:81–91, 1990.

Podlecki et al. Nuclear translation of the insulin receptor. *J. Biol. Chem* 1987, 262:3362.

Nakata et al. Cloning and characterization of gastrin receptor. *Biochem Biophys Res Commun.* 1992 187:1151.

Curtis et al. IL–1 and its receptor . . . *J. Immunol.* 144:1295–1303.

Seva et al. Growth–promoting effects . . . *Science* 265:410 (1994).

Singh, P. et al. Novel gastrin receptors . . . *J. Biol. Chem.* 270:8429–35, 1995.

Fourmy et al. Relationship of CCK/gastrin receptor binding . . . *Regulatory Peptides* 10 (1984) 57–68.

Kopin et al. Expression, cloning and characterization of the canine perietal cell gastrin receptor. *Proc Natl. Acad. Sci. USA* 89 (1992) 3605–3609.

Taniguchi et al. Cholecystokinin–B/gastrin receptor signaling pathway. *Oncogene* 1994 9:861–867.

Le Meuth et al. Differential expression. *Endocrinology* 133:1182–1191 (1993).

Dickinson. Relationship of gastrin processing . . . *Gastroenterology* 109:1384–8.

Johnson. New aspects of the trophic action . . . *Gastroenterology* 72:788–792 (1977).

Grider. Distinct receptors for cholecystokinin and gastrin . . . *Am J. Physiol* (1990) 259:G184.

Matsumoto et al. Gastrin receptor . . . *Am. J. Physiol* 252:G143 (1987).

Laduron. From receptor internalization . . . *Biochem Pharm* (1994) 47:3–13.

Ullrich et al. Signal transduction by receptors. *Cell* (1990) 61:203–212.

Hughes et al. Development of a class of . . . CCK–B receptor antagonists . . . *PNAS (USA)* 87:6728.

Rehfeld et al. Gastrin in human bronchogenic carcinomas. *Cancer Res* (1989) 49:2840.

Beinborn et al. A single a. a. of the CCKB/gastrin receptor . . . *Nature* 362 (1993).

Watson et al. Gastrin receptors . . . *Medical Intelligence Unit* pp. 1–99 R.G. Landes & Co. Austin TX CRC 1993.

Article by Watson et al. "Gastrin antagonists" Invest Drugs (1995) 4:1253.

Tarasova et al. "Anti–peptide antibodies specific for the gastrin–cholecystokinin–B receptor." Letters in Peptide Science 1(5), 1995, 221, (X P002077684).

Helander et al. "Immunohistochemical localization of gastrin/CCK—B receptors in the dog and guinea pig stomach." Acta Physiol.Scand. (1997), 159 (4), 313–320 (XP002077685).

Watson et al. "Expression of gastrin—CCKB receptor isoforms in gastrointestinal tumor" 88th Ann. Meet. An. Assoc. Cancer Rs. San Diego, CA, Proc. 38(0), 1997, 116 Abst.

* cited by examiner

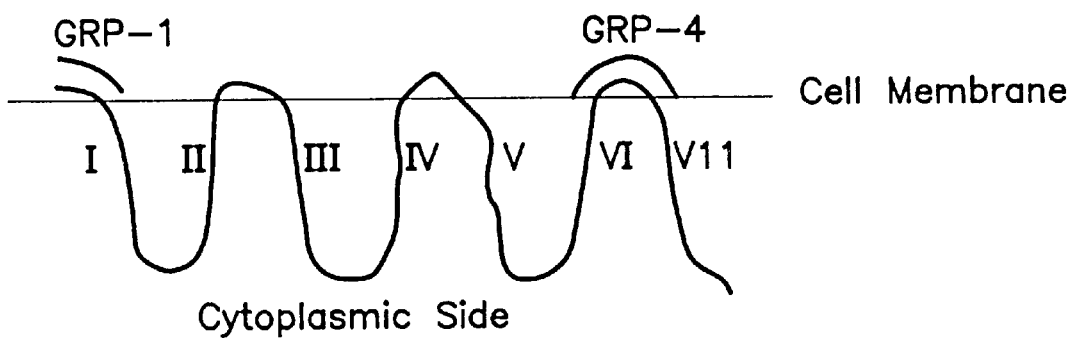
FIG. IA
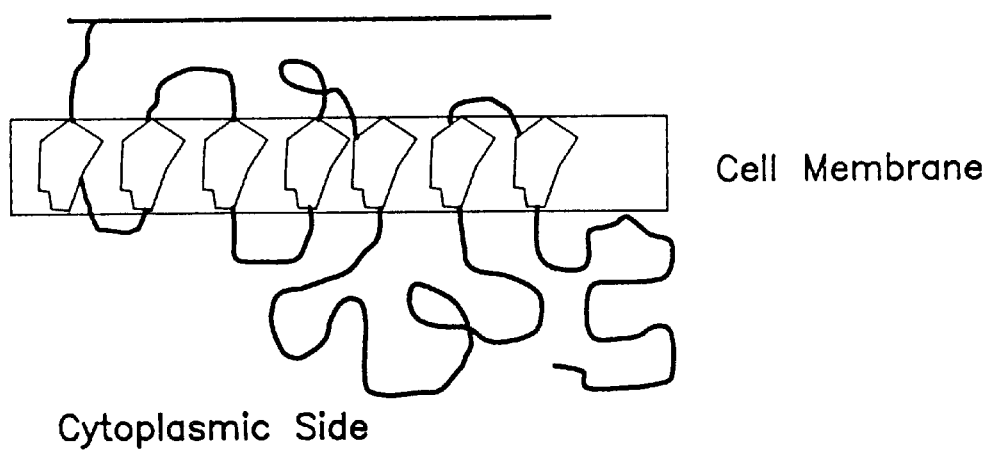
FIG. IB

EVALUATION OF GRP1 IMMUNOREACTIVITY IN
C170HM2 XENOGRAFTS BY WESTERN BLOTTING
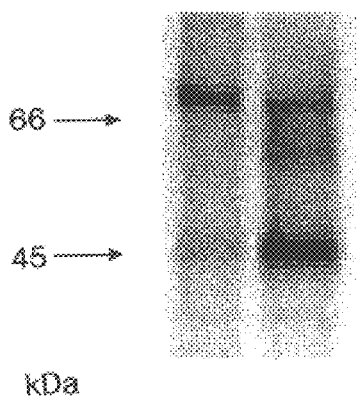
EVALUATION OF GRP1 IMMUNOREACTIVITY IN
170HM2 XENOGRAFTS BY WESTERN BLOTTING
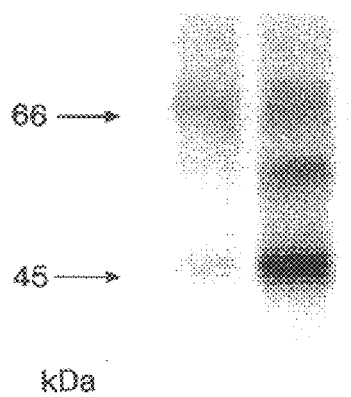
FIG. 23

HISTOLOGICAL ANALYSIS OF C170HM2 TUMORS

APOPTOTIC CELLS WERE EVIDENT IN THE VIABLE
TUMOR IN RABBIT ANTI-GRP1 TREATED GROUP

IMMUNOGENIC COMPOSITIONS TO THE CCK-B/GASTRIN RECEPTOR AND METHODS FOR THE TREATMENT OF TUMORS

CROSS REFERENCE TO RELATED APPLICATION

This application claims the benefit under 35 U.S.C. §119 (e), of U.S. Provisional Application No. 60/046,201 filed on May 12, 1997.

BACKGROUND OF THE INVENTION

The hormone gastrin binds to a gastrin/cholecystokinin (CCK)-B receptor with high affinity via its 5 carboxy-terminal amino acids. The CCK-B/gastrin receptor is a cytoplasmic membrane protein which is coupled via a G protein to intracellular signal transduction pathways that in turn control the expression of various genes.

Gastrin is a peptide hormone which occurs in two forms, tetratriacontagastrin (G34) and heptadecagastrin (G17), and is synthesized and secreted by specialized cells, G cells, that are located in the stomach antrum. The hormone is secreted into the circulating blood and binds to specific cells in the stomach, namely, enterochromaffin-like (ECL) and parietal cells, that indirectly or directly affect stomach acid output. Historically, gastrin hormones have been associated with the stimulation of gastric acid secretion (Edkins, J. S. 1905). (The full citations for the references cited herein are provided in the Reference section preceding the claims.) In recent years, evidence has accumulated that gastrin may act as a trophic factor within the gastrointestinal tract (Johnson, L. 1997) and that it can promote the growth of gastrointestinal cancers (Watson et al. 1989, Dickinson, C. J. 1995), as well as non-gastrointestinal cancers including small cell carcinoma of the lung (Rehfeld et al. 1989). In the post-translational processing of gastrin, it is the "mature" carboxy-amidated form that binds to the gastrin/CCK-B receptor via the carboxy terminus (Kopin et al. 1992).

It has been shown that several types of tumors, e.g., colorectal, stomach, pancreatic and hepatocellular adenocarcinomas possess CCK-B/gastrin receptors in their plasma membranes and that they respond to gastrin with powerful cellular proliferation (Rehfeld, J. F. 1972, Upp et al. 1989 and Watson et al. 1993). Furthermore, more recently it has been discovered that many of these cancer cells also secrete gastrin and thus effect an autonomous proliferative pathway (Van-Solinge et al. 1993, Nemeth et al. 1993 and Seva et al. 1994).

The CCK-B/gastrin receptor belongs to a family of G protein-coupled receptors with seven transmembrane domains with equal affinity for both CCK and gastrin (Soll et al. 1984). This receptor was named a CCK type-B receptor because it was found predominantly in the brain (Wank et al. 1992). The receptor was subsequently found to be identical to the peripheral CCK/gastrin receptor in the parietal and ECL cells of the stomach (Nakata et al. 1992). This receptor has been well characterized in a number of normal (Fourmy et al. 1984, Grider et al. 1990) and tumor tissues (Singh et al. 1990, Watson et al. 1993), and extensively studied using the rat pancreatic adenocarcinoma cell line AR42J (Scemama et al. 1987). The AR42J CCK-B/gastrin receptor cDNA has been cloned and sequenced, and it is more than 90% homologous in DNA sequence to the CCK-B/gastrin receptor in rat and human brain, and more than 84% homologous in sequence to the canine parietal cell CCK-B/gastrin receptor cDNA (Wank, S. A. 1995), demonstrating a high sequence homology even between species.

The peptide hormones G17 and G34 bind to the CCK-B/gastrin receptor on the cell membrane of normal cells. However, it has been found that G17, and not G34, stimulates the growth of gastrin-dependent cancer cells. Serum-associated G17, in particular, has the potential to stimulate the growth of colorectal tumors in an endocrine manner mediated by CCK-B/gastrin receptors (Watson et al. 1993) in the tumor cells. Gastrin-17 appears to be particularly implicated in stimulating the growth of colorectal adenocarcinomas due to a possible increased affinity for the CCK-B/gastrin receptor on the tumor cells, over other gastrin hormone species (Rehfeld 1972 and 1993). The CCK-B/gastrin receptors were found to be expressed in a high affinity form on 56.7% of human primary colorectal tumors (Upp et al. 1989). It has been postulated that a potential autocrine loop may also exist due to endogenous production of precursor gastrin peptides by such tumors (Van-Solinge et al. 1993 and Nemeth et al. 1993). The resulting G17 ligand/receptor complex stimulates cell growth by way of secondary messengers for regulating cell function (Ulirich et al. 1990). The binding of G17 to the CCK-B/gastrin receptor leads to activation of phosphatidyl inositol breakdown, protein kinase C activation with a resultant increase in intracellular calcium ion concentration, as well as the induction of c-fos and c-jun genes via mitogen-activated protein kinase, which has been implicated in the regulation of cell proliferation (Tadisco et al. 1995). Additionally, gastrin binding to the CCK-B/gastrin receptor has been associated with the subsequent increase in phosphorylation by a tyrosine kinase, pp125FADK (focal adhesion kinase), which may also have a role in the transmission of mitogenic signals (Tanaguchi et al. 1994).

A number of high affinity CCK-B/gastrin receptor antagonists have been evaluated therapeutically both in vitro and in vivo in a number of experimental gastrointestinal cancers. For example, proglumide, a glutamic acid derivative (Seva et al. 190; Harrison et al. 1990 and Watson et al. 1991a); Benzotript, an N-acyl derivative of tryptophan; L-365,260, a derivative of Aspercillin (Bock et al. 1989), and CI-988 a molecule that mimics the C-terminal pentapeptide sequence of CCK (Hughes et al. 1990) have been shown to effectively neutralize the effects of exogenous gastrin on gastrointestinal tumor growth both in vitro and in vivo (Watson et al. and Romani et al. 1994). However, these antagonists have severe toxic side effects and lack specificity as they block the action of all potential ligands of the receptor such as G34 and CCK in normal cells. Recently, highly potent and selective CCKB/gastrin receptor antagonists such as YM022 (Yuki et al., 1997) and YF476 (Takinami et al., 1997) have been also described.

Proglumide and Benzotript have been widely assessed in the pre-clinical studies. The main problem with these compounds is their lack of potency, with relatively high concentrations required to displace G17 (Watson et al., 1992a; Watson et al., 1992b). Despite this, proglumide and benzotript inhibited the basal and gastrin-stimulated proliferation of a number of cell lines (Seva et al., 1990; Watson et al., 1991a). In addition, proglumide increased the survival of xenograft mice bearing the gastrin-sensitive mouse colon tumor, MC26 to 39 days in the treated animals from 25 days in the control animals.

Due to the low specificity of this class of gastrin antagonising agents for the gastrin/CCKB receptor, the inhibition of tumor growth may not be effectively control with gastrin antagonists. Moreover, the cellular receptors which recognize and bind the gastrins do not bind all the inhibitors tested (Seva et al. 1994). Thus, if complete inhibition of gastrin binding to the receptor does not occur in the autocrine growth cascade, then the gastrin antagonists may be unable to block this mechanism of tumor growth promotion.

SUMMARY OF THE INVENTION

The present invention provides immunogenic compositions and immunological methods for the treatment of gastrin-dependent tumors. The method comprises the active or passive immunization of a patient with an anti-CCK-B/gastrin receptor immunogen or anti-CCK-B/gastrin receptor antibodies. The antibodies produced by the immunogens are specific against the CCK-B/gastrin receptor on tumor cells and block the growth-promoting effects of gastrin on the receptors. The antibodies prevent the peptide hormones from binding to the CCK-B/gastrin receptors on gastrin-dependent tumor cells; thus, the growth of the tumor is arrested. Furthermore, surprisingly, the antibodies specific to the $NH_2$-terminal end of the receptor, upon binding to the receptor, are internalized and rapidly translocated into the cytoplasm and into the nucleus of the tumor cells. This internalization can occur as early as 10 seconds after exposing the cells to the antibody. This rapid internalization of the antibody/receptor complex in turn causes the affected tumor cells to undergo apoptosis or suicide.

The immunogens of the invention comprise natural or synthetic peptides derived from the human CCK-B/gastrin receptor, as the immunomimic portion of the immunogen. The immunogens may also comprise a spacer peptide sequence attached to an end of the immunomimic peptide. The immunogen may also be conjugated to a protein carrier, such as Diphtheria toxoid, tetanus toxoid, bovine serum albumin and the like.

In one embodiment, the method of immunization against the CCK-B/gastrin receptor comprises active immunization, wherein a patient is immunized with an immunogen of the invention. The immunogen stimulates the production of antibodies against the CCK-B/gastrin receptor on tumor cells.

The antibodies produced by the anti-CCK-B/gastrin receptor immunogens bind to the CCK-B/gastrin receptors on tumor cells and effectively prevent the binding of the peptide hormones to the receptors, thereby inhibiting the autocrine growth-stimulatory pathway of tumor cell division and ultimately the growth of the tumor.

In another embodiment of the invention, the method of treatment comprises passive immunization, whereby antibodies against the CCK-B/gastrin receptor are administered to a patient in a sufficient concentration to bind to the CCK-B/gastrin receptors of the tumor cells, and the antibodies block the binding of the peptide hormones to the receptor. The prevention of binding of the hormones to their receptor inhibits the growth-stimulus pathway of the tumor cells, thereby inhibiting the growth of the hormone-dependent tumors. In a preferred embodiment of this aspect of the invention, the antibodies for human therapy may be chimeric, humanized, or human monoclonal antibodies which may be produced by methods well known in the art. In addition, the anti-CCK-B/gastrin receptor antibodies may be further conjugated to cytotoxic molecules such as cholera toxin, or to radioactive molecules labeled with a radionuclide, such as $^{125}I$ and $^{131}I$, to enhance the killing of the tumor cells.

The invention also provides a method for diagnosing a gastrin-responsive tumor, comprising the immunochemical detection of gastrin-dependent (CCK-B/gastrin-containing) tumors from a tissue biopsy using the antibodies of the invention. The specific anti-CCK-B/gastrin receptor antibodies of the invention can be labeled with a detection system utilizing compounds such as biotin, horseradish peroxidase and fluorescein to detect the CCK-B/gastrin receptors in the tumor tissue using standard immunochemical procedures.

The invention also provides a method for diagnosing a gastrin-dependent tumor, comprising the in vivo detection of gastrin-dependent (CCK-B/gastrin receptor-containing) tumors, using the anti-CCK-B/gastrin receptor antibodies. The method comprises, administering to a patient possessing a colorectal tumor an effective dose of radiolabeled anti-CCK-B/gastrin receptor antibodies via an intravenous injection, and imaging or detecting tumor cells having anti-CCK-B/gastrin receptor antibodies bound to their cell membranes by standard scintigraphic scanning procedures. In this aspect of the invention, the anti-CCK-B/gastrin-receptor-antibodies should be labeled with a radionuclide such as $^{111}Indium$, $^{90}Yttrium$, and $^{131}I$.

BRIEF DESCRIPTION OF THE DRAWINGS

FIGS. 1A and 1B illustrate schematic views of the CCK-B/gastrin receptor and its 7 transmembrane domains.

FIG. 23 depicts Western blots of C170HM2 liver tumor xenograft proteins of control and anti-GRP1-treated nude mice.

DETAILED DESCRIPTION OF THE INVENTION

Figure 2:
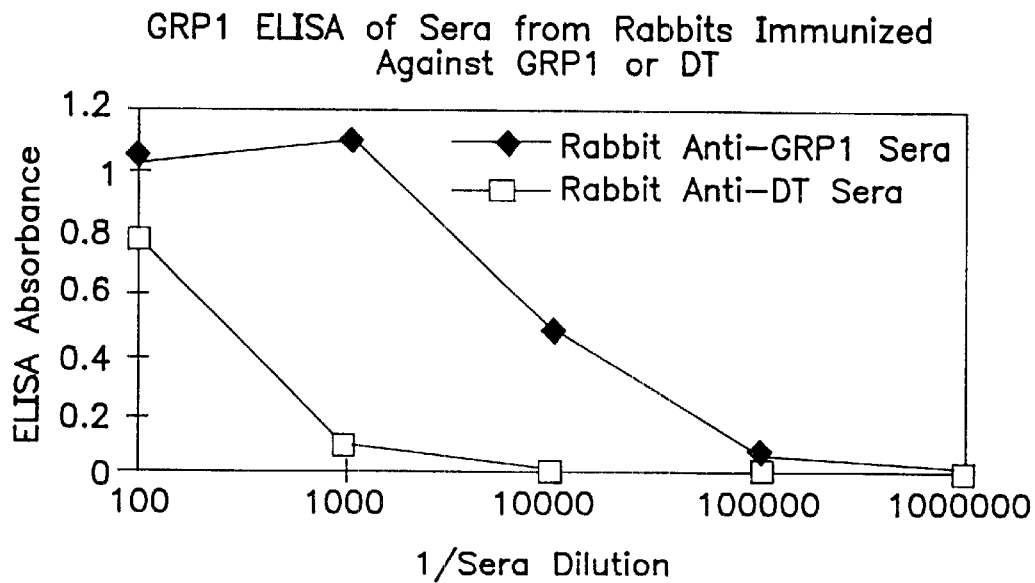
FIG. 2 shows data from ELISA assays with antibodies raised in rabbits immunized with an immunogen against Peptide 1 of the CCK-B/gastrin receptor.

The methods of the invention are directed to the treatment of gastrin hormone-dependent tumors in animals, including humans, and comprise administering to a patient an anti-CCK-B/gastrin-receptor immunogen, which produces antibodies in the immunized patient which bind to the CCK-B/gastrin-receptor on the tumor cells, so as to prevent the binding of the hormone to the receptor in order to inhibit the growthpromoting effects of the hormone. More importantly, from a clinical point of view, the receptor/anti GRP1 complex is rapidly internalized, traverses the cytoplasm and enters the nucleus. This apparently triggers the affected tumor cells to commit suicide (apoptosis).

The immunogens comprise natural or synthetic peptides of the human CCK-B/gastrin-receptor which act as immunomimics. In particular, two synthetic peptides have been developed as the immunomimics. These peptides, developed from the amino acid sequence of the CCK-B/gastrin-receptor, are immunogenic and cross-reactive with the endogenous CCK-B/gastrin-receptor of tumor cells both in vivo and in vitro. Peptide 1 consists of amino acids 5 through 21 of the CCK-B/gastrin-receptor sequence: KLNRSVQGT-GPGPGASL (Peptide 1, SEQ ID NO.: 1 in the Sequence Listing). Peptide 1 constitutes the amino-terminal end of the receptor and is located on the extracellular surface of the cell membrane (see FIG. 1).

In another embodiment, the immunogen comprises Peptide 4, which consists of the following amino acid sequence of the CCK-B/gastrin-receptor: GPGAHRALSGAPISF (Peptide 4, SEQ ID NO.: 2 in the Sequence Listing). Peptide 4 is part of,the fourth extracellular domain of the receptor and it too is on the outer side of the plasma membrane (see FIG. 1).

The immunogens may also comprise an extension or spacer peptide suitable for projecting the immunomimic peptide away from the protein carrier and enhancing its capacity to bind the lymphocyte receptors. A suitable spacer peptide sequences the amino acid sequence SSPPPPC (Serine (Ser) spacer, SEQ ID NO.:3 in the Sequence Listing). However other spacer peptides would be suitable as well. The immunomimic peptides, with or without the spacer, are then conjugated to a protein carrier, such as Diphtheria toxoid, via a cysteine residue at the carboxy terminal end. The spacer peptides are not immunologically related to the CCK-B/gastrin-receptor-derived peptides and should therefore enhance, but not determine, the specific immunogenicity of the receptor-derived peptides.

The presence and density of CCK-B/gastrin-receptors on tumor cells in a patient can be determined by reacting labeled anti-receptor antibodies with a sample of obtained from tumor biopsy sample. The anti-receptor antibodies can be labeled with either a radioactive tracer, a dye or a fluorescent label. In addition, the responsiveness of the tumor. cells to gastrin can be evaluated in vitro from a tumor biopsy sample of the patient using standard techniques. Patients having tumors with biopsy samples positive for the CCK-B/gastrin-receptor antibody assay are typical candidates for treatment by the methods of the invention.

An effective dosage ranging from 0.001 to 2 mg of the immunogenic composition is administered to the patient for the treatment of the gastrointestinal cancer. The effective dosage of the immunogenic composition should be capable of eliciting an immune response in a patient consisting of effective levels of antibody titer against the CCK-B/gastrin-receptor 1–3 months after immunization. Following the immunization of a patient, the effectiveness of the immunogens is monitored by standard clinical procedures, such as ultrasound and magnetic resonance imaging (MRI), to detect the presence and size of tumors. The antibody titer levels against the receptor may also be monitored from a sample of blood taken from the patient. Booster immunizations should be given as required to maintain an effective antibody titer. Effective treatment of gastrin-dependent cancers, such as stomach, liver, pancreatic and colorectal adenocarcinomas, according to this method should result in inhibition of tumor growth and a decrease in size of the tumor.

The antibodies raised by the anti-CCK-B/gastrin-receptor immunogens of the present invention may have anti-trophic effects against gastrin-dependent tumors by three potential mechanisms: (i) inhibition of gastrin binding to its receptor, (ii) degradation or disruption of the signal transduction pathway of tumor cell proliferation; and (iii) induction of apoptosis (or cell suicide) in cells where receptor/antibody complexes are internalized and migrate into the nucleus.

In another embodiment of the invention, anti-CCK-B/gastrin-receptor antibodies are administered to a patient possessing a CCK-B/gastrin-receptor-responsive tumor. The antibodies specifically bind to the CCK-B/gastrin-receptors on the tumor cells. The binding of the antibodies to the receptors prevents the binding of gastrin to its ligand in the membranes of cells and, therefore, the growth signal for the gastrin-dependent tumor cells is inhibited and the growth of the tumor is arrested. The antibodies are preferably chimeric or humanized antibodies, or fragments thereof, which effectively bind to the target receptor and may be produced by standard techniques such as those disclosed in U.S. Pat. Nos. 5,023,077, 5,468,494, 5,607,676, 5,609,870, 5,688,506 and 5,662,702, the disclosures of which are hereby incorporated by reference. These exogenously produced antibodies may also be useful for killing tumor cells that bear the CCK-B/gastrin-receptor on their plasma membranes by virtue of their inhibiting the growth of the tumor cells or delivering a toxic substance to the tumor cell. Preferred anti-CCK-B/gastrin antibodies for therapy are those reactive with extracellular domains 1 and 4 of the receptor protein shown in FIG. 1 as GRP-1 and GRP-4, respectively. Particularly preferred are, antibodies which specifically recognize and bind amino acid sequences of the receptor protein corresponding to Peptides 1 and 4. The inhibition of tumor growth in this method of immunization is also monitored by ultrasound imaging and MRI and repeated immunizations are administered as required by the patient.

The effectiveness of the antibodies in inhibiting tumor cell growth and killing of tumor cells can be enhanced by conjugating cytotoxic molecules to the anti-CCK-B/gastrin antibodies. The cytotoxic molecules can be toxins, for example, cholera toxin, ricin, α-amanitin, or radioactive molecules labeled, for example with $^{125}$I or $^{131}$I, or chemotherapeutic agents, for example, cytosine arabinoside or 5-fluorouridine.

In addition to antibodies radiolabeled with $^{125}$I and $^{131}$I, the anti-CCK-B/Gastrin-receptor antibodies can also be labeled with radionuclide such, as $^{111}$Indium and $^{90}$Yttrium. In this aspect of the invention the antibodies are useful for the detection and diagnosing of CCK-B/gastrin-receptor possessing tumors in vivo, by administering these antibodies to the patient, and detecting bound antibodies on CCK-B/gastrin-receptor-containing tumor cells. After allowing the radiolabeled anti-CCK-B/gastrin antibodies to reach the tumor, about 1–2 hours after injection, the radioactive, "hot spots" are imaged using standard scintigraphic procedures as previously disclosed (Harrison's Principles of Internal Medicine, Isselbacher et al. eds. 13$^{th}$ Ed. 1994).

The compositions in which the immunogens are administered for the treatment of gastrin-dependent tumors in patients may be in a variety of forms. These include, for example, solid, semi-solid and liquid dosage forms, such as powders, liquid solutions, suspensions, suppositories, and injectable and infusible solutions. The preferred form depends on the intended mode of administration and therapeutic applications. The compositions comprise the present immunogens and suitable pharmaceutically acceptable components, and may include other medicinal agents, carriers, adjuvants, excipients, etc. Suitable adjuvants may include nor-muramyl dipeptide (nor-MDP, Peninsula Labs., Calif.), and oils such as Montanide ISA 703 (Seppic, Inc., Paris, France), which can be mixed using standard procedures. Preferably, the compositions are in the form of unit dose. The amount of active compound administered for immunization or as a medicament at one time, or over a period of time, will depend on the subject being treated, the manner and form of administration, and the judgment of the treating physician.

The anti-CCK-B/gastrin-receptor antibodies of the invention for passive immunization are preferably administered to a patient intravenously using a pharmaceutically acceptable carrier, such as a saline solution, for example, phosphate-buffered saline.

EXAMPLE 1

Preparation of GRP1-DT and GRP4-DT Conjugates

CCK-B/gastrin-receptor peptides were prepared by standard solid state peptide synthesis. To make immunogens capable of inducing specific immune responses each of Peptide 1 and 4 was synthesized containing the spacer sequence SSPPPPC (SEQ ID NO.:3 in the Sequence Listing) at its carboxy terminus. These peptides were subsequently conjugated to amino groups present on the carrier, Diphtheria toxoid ("DT"), via the terminal peptide amino acid residue cysteine of the spacer utilizing a heterobifunctional linking agent containing a succinimidyl ester at one end and maleimide at the other end of the linking agent by either of Method A or Method B as described below.

Method A: As previously described in U.S. Pat. No. 5,023,077, the linking of Peptide 1 or 4 above and the carrier is accomplished as follows. Dry peptide was dissolved in 0.1 M Sodium Phosphate Buffer, pH 8.0, with a thirty-fold molar excess of dithiothreitol ("DTT"). The solution was stirred under a water saturated nitrogen gas atmosphere for four hours. The peptide containing reduced cysteine was separated from the other components by chromatography over a G10 Sephadex column equilibrated with 0.2 M acetic acid. The peptide was lyophilized and stored under vacuum until used. The carrier was activated by treatment with the heterobifunctional linking agent e.g. Epsilon-maleimidocaproic acid N-hydroxysuccinimide ester, ("EMCS"), in proportions sufficient to achieve activation of approximately 25 free amino groups per $10^5$ molecular weight of carrier. In the specific instance of diphtheria toxoid, this amounted to the addition of 6.18 mg of EMCS (purity 75%) to each 20 mg of diphtheria toxoid.

Activation of diphtheria toxoid was accomplished by dissolving each 20 mg aliquot of diphtheria toxoid in 1 ml of 0.2 M Sodium Phosphate Buffer, pH 6.45. Aliquots of 6.18 mg EMCS were dissolved into 0.2 ml of Dimethyl Formamide ("DMF"). Under darkened conditions, the EMCS was added dropwise in 50 microliter ("$\mu l$") amounts to the DT with stirring. After 2 hours of incubation in darkness, the mixture was chromatographed on a G50 Sephadex column equilibrated with 0.1 M Sodium Citrate buffer, pH 6.0, containing 0.1 mM EDTA.

Fractions containing the EMCS activated diphtheria toxoid were concentrated over a PM 10 ultrafiltration membrane under conditions of darkness. The protein content of the concentrate was determined by either the Lowry or Bradford methods. The EMCS content of the carrier was determined by incubation of the activated carrier with cysteine-HCl followed by reaction with 10 mM of Ellman's Reagent 5,5'dithio-bis (2-nitrobenzoic acid) 10 mM. The optical density difference between a blank tube containing cysteine-HCl and the sample tube containing cysteine-HCl and carrier was translated into EMCS group content by using the molar extinction coefficient of $13.6 \times 10^3$ for 5-thio-2-nitrobenzoic acid at 412 nm.

The reduced cysteine content (—SH) of the peptide was also determined utilizing Ellman's Reagent. Approximately 1 mg of peptide was dissolved in 1 ml of nitrogen gas saturated water and a 0.1 ml aliquot of this solution was reacted with Ellman's Reagent. Utilizing the molar extinction coefficient of 5-thio-2-nitrobenzoic acid ($13.6 \times 10^3$, the free cysteine —SH was calculated. An amount of peptide containing sufficient free —SH to react with each of 25 EMCS activated amino groups on the carrier was dissolved in 0.1 M Sodium Citrate Buffer, pH 6.0, containing 0.1 mM EDTA, and added dropwise to the EMCS activated carrier under darkened conditions. After all the peptide solution had been added to the carrier, the mixture was incubated overnight in the dark under a water-saturated nitrogen gas atmosphere.

The conjugate of the peptide linked to the carrier via EMCS was separated from other components of the mixture by chromatography over a G50 Sephadex column equilibrated with 0.2 M Ammonium Bicarbonate. The conjugate eluted in the column void volume was lyophilized and stored desiccated at 20° C. until used.

The resulting conjugate may be characterized as to peptide content by a number of methods known to those skilled in the art including weight gain, amino acid analysis, etc. Conjugates of Peptides 1 and 4 with spacer and diphtheria toxoid produced by this method were determined to have an effective peptide/carrier ratio of 5–35 moles of peptide per 100 KD MW of carrier and all were considered suitable as immunogens for immunization of test animals. Preferably, the range of the peptide from 10–30 moles per 100 KD MW of DT produced an effective immune response.

Method B: In a preferred method, conjugates comprising GRP1 coupled to DT and GRP4 peptide coupled to DT were prepared at room temperature as follows. Purified DT (400 mg) was dissolved in 20 ml of 0.5 M phosphate buffer, pH=6.6, saturated with nitrogen gas to give a DT solution of 20 mg/ml. The DT solution was placed in a 60 ml dark amber glass bottle (serving as a reaction vessel and filtration reservoir). EMCS coupling reagent (123.6 mg) was dissolved in 2.0 ml of dimethylformamide. The EMCS solution was added dropwise to the DT solution over a 15 minute period with continuous stirring. The bottle was capped, and the mixture was stirred at room temperature for an additional 1 hour 45 minutes, to form activated DT (M-DT). The M-DT was then purified by diafiltration using an Amicon Model TFC10 Thin-Channel Ultrafiltration System per operating manual I-113G with a XM50 diaflow ultrafiltration membrane. The M-DT was washed twice against volumes of 420 ml phosphate buffer, concentrating to 20 ml each time, then washed once against 420 ml of 0.1 M sodium citrate buffer, pH=6.0, containing 0.1 M EDTA, and concentrating the solution down to 20 ml.

To make GRP1-DT conjugate, 2.02 ml of M-DT solution (containing 22.3 mg M-DT) was placed in a 10 ml dark amber glass vial, then 13 mg of GRP 1 peptide was dissolved in the citrate buffer to give 40 mg/ml peptide and added dropwise to the M-DT solution with stirring. To make GRP4-DT conjugate, 2.21 ml of M-DT solution (containing 24.4 mg M-DT) was placed in a 10 ml dark amber glass vial, then 13 mg of GRP4 peptide was dissolved in the citrate buffer to give 40 mg/ml peptide and added dropwise to the M-DT solution with stirring.

The reactions were allowed to proceed overnight in the dark. Each conjugate was removed from the reaction vessels and separately dialyzed in 12,000–14,000 MW cutoff dialysis tubing against 5 changes 500 ml of 0.1 M ammonium bicarbonate solution. Each conjugate was lyophilized. The conjugates were then analyzed by amino acid analysis and their peptide to DT substitution ratios were determined to be 21.8 peptides per $10^5$ MW of DT for GRP1-DT and 21.1 peptides per $10^5$ MW of DT for GRP4-DT.

Conjugates of Peptides 1 and 4 with spacer and DT produced by this method have an effective peptide/carrier ratio of 5–35 moles of peptide per 100 KD MW of carrier and all are considered suitable as immunogens. A preferred ratio range for producing an effective immune respose is from 10–25 moles of peptide per 100 KD MW of DT.

Preparation of Immunogens

The present immunogens containing either Peptide 1 or Peptide 4 with spacer conjugated to DT as described above were used to immunize rabbits. Immunogens were prepared as follows: Conjugate was dissolved in 0.15 M Sodium phosphate buffered saline, pH 7.3 to a concentration of 3.79 mg/ml. The conjugate solution was added to Montanide ISA (703) Adjuvant (Seppic, Inc.) in a 30:70 (wt:wt) ratio of conjugate solution to Montanide ISA 703, then the mixture was homogenized using a Silverson Homogenizer for 3 minutes at 8,000 RPM to form an emulsion containing 1 mg/ml of conjugate.

Immunization and Sample Collection

Rabbits were injected intramuscularly with 0.1 ml of immunogen consisting of 0.1 mg of either GRP1-DT, or GRP4-DT conjugate. Each rabbit was given injections of immunogen at 0 and 4 weeks. Blood was collected from each rabbit at 6 and 8 weeks of the experiment. Serum was prepared from each blood sample and stored at −20° C. until utilized in assays to determine the presence of anti-CCK-B/gastrin-receptor antibodies.

Enzyme-Linked Immunosorbent Assay (ELISA)

A solid-phase ELISA was used to screen for reaction or cross-reaction of antisera raised against Peptide 1 and Peptide 4 of each immunized rabbit. The ELISA was carried out by coating polystyrene 96 well plates (IMMOLON 11, Dynatech) with 25 $\mu$l/well of 10 $\mu$g/ml of Peptide 1 linked to bovine serum albumin (BSA) ("GRP1-BSA"), or Peptide 4 linked to BSA ("GRP4-BSA") antigen in 0.1 M Glycine-HCl, pH 9.5 buffer. The plates were incubated overnight at 4° C., and subsequently washed in buffer.

Antisera obtained from the immunized rabbits were serially diluted to a range of $10^{-1}$ to $10^{-8}$ in 1% BSA-FTA hemagglutination buffer, pH 7.2. Twenty five $\mu$l of test antiserum per well was incubated with each test peptide for 1 hr at room temperature. After incubation, the plates were washed thoroughly with buffer to remove any unbound antibody. Each well was treated with 25 $\mu$l of biotinylated goat anti-rabbit IgG (H+L) diluted 1:1000 in 1% BSA-FTA dilution buffer for 1 hour at room temperature. After washing the plates to remove unbound anti-rabbit reagent, each well was incubated for 1 hour at room temperature with 25 $\mu$l of avidin-alkaline phosphatase conjugate diluted 1:1000 in 1% BSA-FTA buffer. The plates were washed thoroughly to remove unbound avidin-alkaline phosphatase reagent, and incubated with 25 $\mu$l of 1 mg/ml of p-nitrophenylphosphate ("PNPP") in 10% diethanolamine buffer containing 0.01% $MgCl_2.6H_2O$, pH 9.8. The plates were allowed to develop until the absorbance of the reaction at 490 nm wavelength reached an optical density between 0.8 to 1.5. To test the specificity of the antisera produced by the rabbits, rabbits were also immunized with DT and for ELISA testing, plates were coated with DT as antigen to determine the reactivity of the antisera produced against the carrier.

Figure 3:
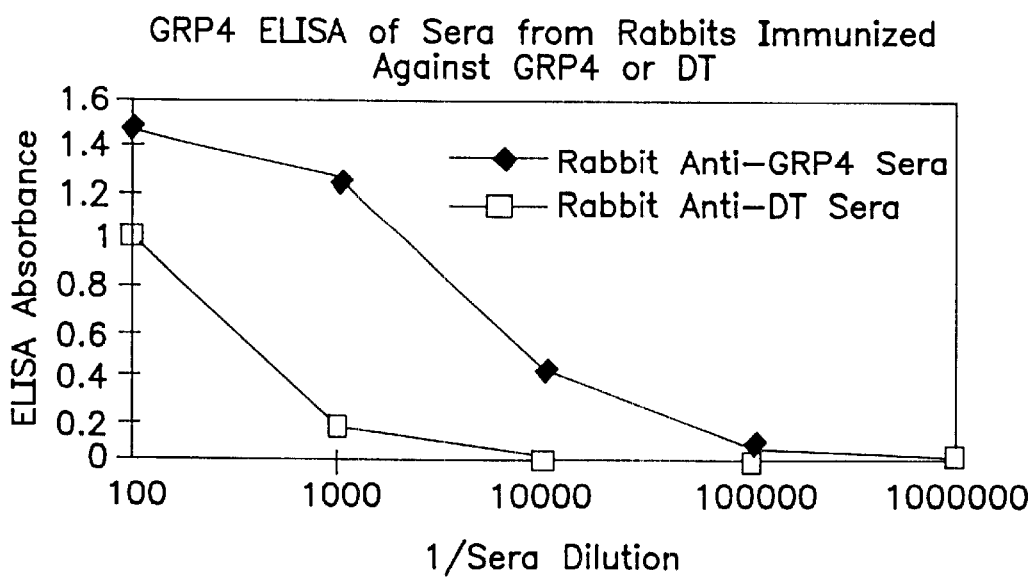
FIG. 3 shows data from ELISA assays with antibodies raised in rabbits immunized with an immunogen against Peptide 4 of the CCK-B/gastrin receptor.

FIG. 2 shows the ELISA results using Peptide 1/GRP1 and FIG. 3 shows the ELISA results using Peptide 4/GRP4 as the antigen. As seen in FIG. 2, the ELISA results show that the rabbits immunized with Peptide 1-spacer-DT conjugate produced high antibody titers which specifically bind to Peptide 1, as indicated by the antibody binding Peptide 1 even at high (1:100,000) dilutions of the antiserum. Similarly, FIG. 3 shows that rabbits immunized with Peptide 4-spacer-DT conjugate produced high titers of anti-Peptide 4 antibodies. As seen in FIGS. 2 and 3, the rabbits immunized against each peptide produced antibodies which bound specifically to each peptide at small antisera concentration. The data indicate that the anti-Peptide 1 and anti-Peptide 4 antibodies have a large capacity for binding Peptides 1 and 4 of the CCK-B/gastrin-receptor. The data also shows that immunization of rabbits with the present conjugates, elicits powerful immune responses against Peptide 1 and Peptide 4, respectively. In addition, rabbits immunized with either Peptide-1 or Peptide-4 conjugate appeared and behaved normal and did not exhibit any symptoms of disease or pathologies during the experiments.

EXAMPLE 2

The following experiments were performed to establish the specificity of antibodies raised in rabbits against the GRP1-DT peptide containing Ser spacer described Example 1 using Method B. A series of tests were conducted to assess the specificity of rabbit antibodies induced by immunization with the GRP1-DT and affinity purified by immunoadsorption over a GRP1-Ser Sepharose column.

An inhibition ELISA was used to assess the specificity of the affinity purified antibodies for GRP1-Ser peptide. The assays were run as follows: GRP1-Ser-BSA conjugate was coated onto 96 well plates (Immulon U bottom) by overnight incubation of 50 µl of a 2 µg/ml solution of conjugate in glycine buffer (0.1M, pH=9.5) at 4° C. Affinity purified anti-GRP1 Ab (at a final concentration of 10 ng/ml) was combined with various inhibitors (in 1:10 dilution series) and incubated for 1 hour at room temperature. The inhibitors included GRP1-Ser, GRP1 EPT, Ser, human gastrin 17(1-9)-Ser spacer (hG17(9)-Ser), GRP1 EPT+Ser, and buffer (no inhibitor). Incubation buffer consisted of PBS+0.5% BSA+0.05% Tween 20+0.02% $NaN_3$. Subsequent steps used the same buffer without BSA. The 96 well plates were washed free of nonbound GRP1-Ser-BSA, and the Ab+inhibitor mixtures were added (50 µl/well). After 1 hour, the plates were washed and a goat anti-rabbit Ig (H+L) alkaline phosphatase conjugate (Zymed) was added (1:2000 dilution). After 1 hour incubation, the plates were washed to remove nonbound reagent, and 50 µl/well of pNPP substrate (Sigma) solution (1 mg/ml) was added in substrate buffer (PBS+0.1 mg/ml $MgCl_2$+10% diethanolamine+0.02% $NaN_3$). Following a 60 minute incubation, absorbance was measured on a MRX reader (Dynatech Laboratories). Samples were run in duplicate, and means were calculated for each concentration. Background binding (established with affinity purified rabbit anti-GnRH antibodies) was subtracted from all values, and the % Inhibition relative to no inhibitor added (anti-GRP1 Ab+buffer) was calculated for each inhibitor tested: % Inhibition=$(100)(1-((A_{uninhibited}-A_{inhibited})/A_{uninhibited}))$, where A=Absorbance. The results are shown in FIG. 4.

Figure 4:
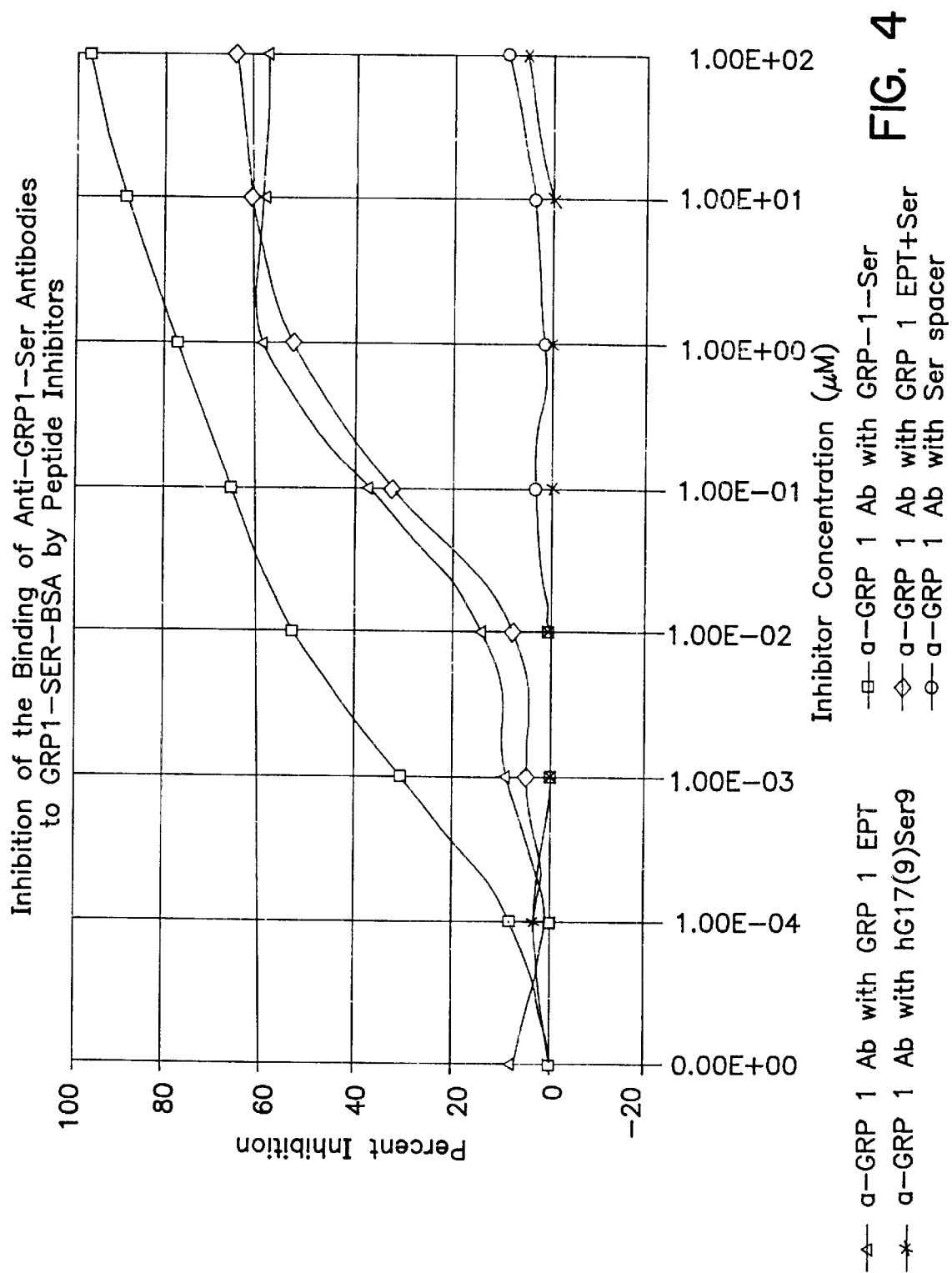
FIG. 4 is a graph showing data obtained from an inhibition ELISA used to assess the specificity of affinity-purified antibodies raised against GRP1-DT immunogen.

FIG. 4 presents the percent inhibition of antibody binding as a function of inhibitor concentration. As can be seen in the figure, the GRP1-Ser peptide fully inhibited antibody binding to GRP1-Ser-BSA. Approximately 60% inhibition was attained with the GRP1 EPT peptide, which does not contain the Ser spacer sequence, and by an equimolar mixture of GRP1 EPT plus Ser spacer. The failure of these peptides to produce full inhibition suggests that a proportion of the antibodies were specific for an epitope(s) comprising elements of both the GRP1 and the Ser spacer sequences. No inhibition was obtained by either the Ser spacer sequence itself or by an unrelated peptide bearing the Ser spacer ("hG17(9)-Ser", consisting of the amino-terminal nine residues of hG17 followed by the Ser spacer). These ELISA results demonstrate that the affinity purified antibody preparation was specific for the GRP1-Ser peptide, and that 60% of the binding activity was directed against the gastrin-receptor epitope component of the peptide.

EXAMPLE 3

AR42J tumor cells (European Collection of Animal Cell cultures, Porton Down, UK) are derived from a rat pancreatic adenocarcinoma and are known to have well characterized CCK-B/gastrin-receptors. Thus AR42J were tested to confirm the expression of CCK-B/gastrin-receptor and specificity of the receptor for hH17 by radioligand inhibition. AR42J cells were cultured at 37° C. with 7% $CO_2$ in complete RPMI 1640 (Sigma) supplemented with 10% FCS (Gemini Bioproducts), 2 mM glutamine (JRH Biosciences), 1 mM sodium pyruvate (JRH B.) and 50 µg/ml gentamicin (Gemini Bioproducts). The cells were harvested from 175 $cm^2$ T-flasks (Falcon Plastics) with PBS containing 0.25% EDTA, then washed twice with PBS (no EDTA) by centrifugation (400×g for 10 min). The cells were kept at 0–4° C. for all manipulations. A single cell suspension was prepared in buffer, and the cell concentration was adjusted to $10^6$ cells/ml. Aliquots of 1 ml of cell suspension were added to 12×75 mm culture tubes, then the cells were centrifuged and the supernatants discarded. The cells were resuspended in PBS (0.1 ml/tube) containing human G17 (hG17), gonadotropin releasing hormone (GnRH), or no peptide. The peptide concentrations were 1.0 ng/ml, 100 ng/ml and 10 µg/ml. An aliquot of 0.1 ml of $^{125}$I-hG17 (NEN), containing approximately 26,300 CPM (specific activity, 2200 Ci/mmol), was added to each tube. The tubes were vortexed, then incubated for 15 minutes. The cells were washed twice with PBS, then counted in a γ counter (Wallac). Samples were run in duplicate. Background counts were subtracted, then the % inhibition of $^{125}$I-hG17 binding by each inhibitor was calculated using the equation: % Inhibition=$(100)(1-((CPM_{uninhibited}-CPM_{inhibited})/CPM_{uninhibited}))$.

Figure 5:
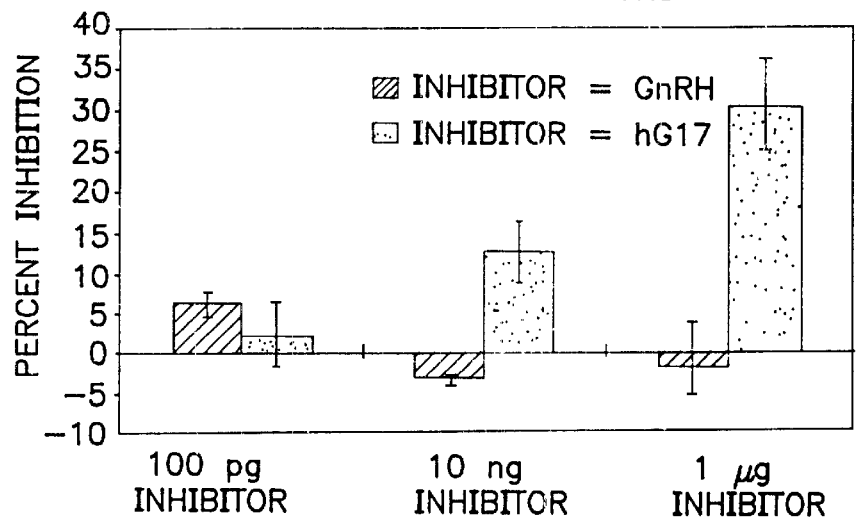
FIG. 5 is a bar graph showing data on the inhibition of the binding of $^{125}I$-human G17 to AR42J cells by peptide inhibitors.

The results of the radioligand binding inhibition tests are shown in FIG. 5, which presents the means (±SE) of the individual values. As can be seen in the figure, binding of $^{125}$I-hG17 to AR42J cells was inhibited by hG17. The degree of inhibition increased with the quantity of inhibitor added, to 32% inhibition at 1 µg hG17 per tube, the highest concentration of peptide tested. Conversely, GnRH produced no inhibition at the two highest concentrations tested (the 6% inhibition obtained with 100 pg GnRH was considered to be nonspecific), indicating that the inhibition by hG17 was specific for gastrin. These results confirmed the cell surface expression of gastrin-receptor by the AR42J tumor cells.

EXAMPLE 4

Binding of the GRP1-Ser specific antibodies to AR42J cells was assessed by immunofluorescence. AR42J cells were grown as in the previous Examples and harvested with cell scrapers from 175 $cm^2$ T-flasks and washed twice with buffer (PBS with 0.02% $NaN_3$) by centrinugation (400×g for 7 min). The cells were kept at 0–4° C. for all manipulations. A single cell suspension was prepared in buffer, and the cell concentration was adjusted to $10^6$ cells/ml. The cell suspension was added to 1.5 ml microfuge tubes (1 ml/tube). The cells were pelleted by centrifugation and supernatants were aspirated. The cells were resuspended in buffer (0.1 ml/tube) containing peptide inhibitors (1.0 mg/ml). The inhibitors included GRP1-Ser, GnRH, hG17(9)-Ser and buffer (no inhibitor). Antibodies, including the rabbit anti-GRP1-Ser (100 µg/ml), affinity purified rabbit anti-DT (negative control, 100 µg/ml), mouse anti-AR42J antiserum (positive control, 1:100 dilution, heat inactivated) or normal mouse serum were added to the appropriate tubes and the contents were mixed. The cells were incubated for 1 hour, with occasional mixing. The cells were then washed three times with buffer, and 0.1 ml of fluorescein-labeled goat anti-rabbit IgG (Antibodies Incorporated) (diluted 1:50) was added per tube. The cells treated with mouse sera were developed with a fluorescein-anti-mouse IgG reagent (Zymed). The cells were re-suspended by vortexing, then incubated for 1 hour. The cells were again washed three times, then re-suspended in glycerol:PBS (1:1, v:v), 50

μl/tube. Wet mounts were prepared with the contents of each tube, and the cells examined using a Laborlux 12 fluorescent microscope (Leitz). Fluorescence was scored on a scale of 0 to 4, with 0 representing background fluorescence (obtained with the normal mouse serum) and 4 representing maximal fluorescence (obtained with the mouse anti-AR42J positive control antiserum).

The results of the immunofluorescesce tests are presented in Table 1. As can be seen in the Table, AR42J cells treated with anti-GRP1-Ser antibodies in the absence of peptide inhibitors fluoresced strongly, indicating that the antibody bound to the cells: Rabbit anti-DT antibodies did not produce fluorescent staining, demonstrating that the staining observed with the anti-GRP1-Ser antibodies was not a consequence of non-specific cell surface binding by rabbit immunoglobulin. Moreover, the binding was shown to be specific for the GRP1-Ser peptide. Addition of GRP1-Ser filly inhibited binding, whereas unrelated peptides, including hG17(9)-Ser and GnRH, failed to inhibit. As the GRP1 epitope comprises residues 5–21 of the gastrin-receptor, it was concluded that the anti-GRP1-Ser antibodies were specific for the gastrin-receptor expressed by AR42J cells.

TABLE 1

| Antibody Preparation | Inhibitor | | | |
|---|---|---|---|---|
| | GRP1-Ser | hG17(9)-Ser | GnRH | Buffer |
| Rabbit anti-GRP1-Ser | 0 | 3+ | 2+ | 3+ |
| Rabbit anti-DT | 0.5+ | 0.5+ | 0.5+ | 0.5+ |
| Mouse anti-AR42J | | | | 4+ |
| Normal Mouse Serum | | | | 0 |

EXAMPLE 5

AR42J cells, passage nos. 16–18 were cultured in RPMI-1640 medium containing 10% FCS and 2 mM glutamine. All cells were maintained at 37° C. in 5% $CO_2$ in air at 100% humidity, grown to 80% conflucency in T75 flasks (Falcon, London, UK) and passage following a 0.02% EDTA treatment to bring adherent cells into suspension. Cells were incubated for 10, 30 seconds, 30 minutes and 1 hour with anti-CCK-B/gastrin-receptor antibody (aGR) generated in rabbits with a CCK-B/gastrin Peptide 1 receptor immunogen of the invention as described in Example 1, which had been purified by affinity chromatography in a column prepared with Peptide 1.

The cells were fixed in 1% glutaraldehyde for one hour and prepared for immunoelectron microscopy (ImmunoEM) studies using standard techniques. The cell suspensions was centrifuged twice at 2000 rpm for 2 minutes and then the cell pellet resuspended in phosphate buffered saline (PBS). The cell pellet was infiltrated with LRwhite plastic resin. Ultrathin sections of 70–90 nm in thickness were cut and place on Pioloform coated nickel grids. The grids were placed in normal goat serum (Dako, High Wycombe, UK) in 0.1% bovine serum albumin (BSA) (Sigma, Poole, Dorset) and incubated at room temperature for 30 minutes. Grids were rinsed in PBS then incubated with a secondary antibody, biotin-conjugated goat anti-rabbit antibody (gold-labelled), diluted 1:50 in 1% BSA, for 1 hour at room temperature. Control experiments were performed without secondary antibody. After final PBS wash, the grids were counterstained in saturated aqueous uranyl acetate for 3 minutes and Reynold's lead citrate for 3 minutes. Gold particles on the cell membrane, in the cytoplasm, on the nuclear membrane and within the nucleus were counted.

Twenty-five cells/grid were counted by an independent observer. For controls AR42J cells were exposed to antibodies for less than 1 second, and liver cells which are devoid of CCK-B/gastrin-receptor were used. AR42J cells exposed to normal IgG were also used as controls for determining non-specific binding of the anti-CCK-B/gastrin-receptor antibodies. The results of these experiments are shown in Table 2 and FIG. 6.

TABLE 2

Distribution of CCK-B/gastrin-receptor Immunogold Particles Within AR42J cells

| | Cell membrane | Cell matrix | Nuclear membrane | Nuclear matrix |
|---|---|---|---|---|
| No. gold particles | 14.2(±0.97) | 43.3(±2.32) | 9.3(±0.81) | 51.4(±3.32) |
| Percent distribution within cell | 12% | 36.6% | 7.9% | 43.5% |

(mean ± SEM for 25 cells, repeated n = 5.)

Figure 6:
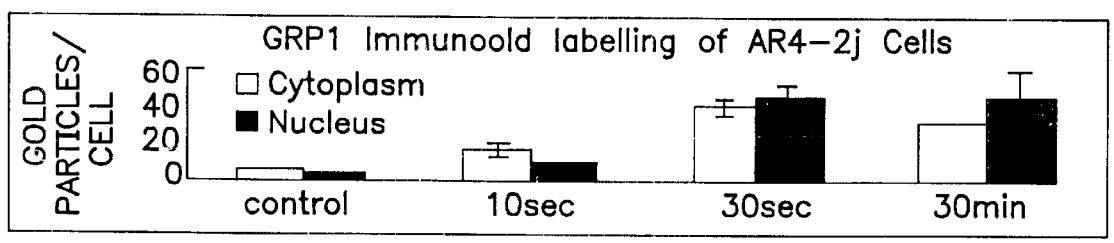
FIG. 6 is a bar graph of the cellular distribution of immunogold-labeled AR4-2J tumor cells.

As demonstrated in Table 2 and FIG. 6, immunogold-antibody particles attached to the CCK-B/gastrin-receptor were localized on plasma membrane, cytoplasm, nuclear membrane, and nuclear matrix of the adenocarcinoma cells, further demonstrating that the antibody/receptor complex is internalized by the cells.

As seen in Table 2, the immunoEM studies using an antiserum directed against the amino-terminal end of the CCK-B/gastrin-receptor shows that after one hour incubation, the distribution of immunogold-labelled CCK-B/gastrin-receptor antibody is quickly internalized as 12% of the antibody receptor complex is associated with the cell membrane, 36.6% is within the cytoplasm, 7.9% is in the nuclear membrane and, quite surprisingly, 43.5% is within the cell nucleus. Areas of intense CCK-B/gastrin-receptor immunoreactivity within the nucleus are found on chromatin, which may suggest specific binding sites for regulation of the DNA.

These electron microscopy studies with anti-immunoglobulin conjugated to gold beads (immmunogold) reveal that an extremely rapid turnover of the anti-receptor/receptor complex occurs in the tumor cells; as early as 10 seconds after exposure to antibodies, complexes are detectable in the cell nucleus as seen in FIG. 6.

EXAMPLE 6

Adenocarcinoma cell lines, namely AR42J, HCT116, C170HM2, LoVo, ST16 and MGLVA1, were grown in vitro and harvested as described in Examples 3. Cells from 30×T-75 flasks were suspended in 5 ml of homogenization buffer (1 mM sodium hydrogen carbonate, 2 mM magnesium chloride, 1 nM phenylmethylsulphonyl fluoride, 40 mM sodium chloride, 10 μl leupeptin, 1 μM pepstatin, 5 nM EDTA [Sigma]). Homogenization was carried out by 5 bursts of 5 second duration in a homogenizer. For extranuclear membranes, tissue debris was pelleted by centrifugation at 500 g, 7 minutes, 4° C. The pellet was discarded and the supernatant centrifuged at 500 g, 4° C. to remove further debris. The supernatant was recentrifuged at 48,000 g, 1 hour, 4° C. The pellet containing the extranuclear membrane preparation was suspended in Tris/NP-40 solution (0.1 M TRIZMA, 0.5% NONIDET P40 [Sigma Chemical]).

For nuclear membrane preparations, following homogenization in a second homogenization buffer (25 mM Tris- HCl, pH 7.4, 0.1% TRITON 100, 0.32 M sucrose, 3 mM MgCl$_2$, 2 mM EGTA, 0.1 mM spermine tetrahydrochloride, 2 mM PMSF, 10 mM bezomidine hydrochloride, 3 mM EGTA aminoacetonitrile hydrochloride [Sigma]), tissue debris was pelleted by centrifugation at 400 g, for 10 minutes at 4° C. The pellet was resuspended in 55% (0.2 M) sucrose in HPLC water. This mixture was spun at 60,000 g for 1 hour at 4° C. The pellet was washed with 0.4% NONIDET P40 in homogenization buffer without TRITON 100. The pellet was spun at 700 g for 15 min at 4° C. and resuspended in homogenization buffer without TRITON 100.

Protein content is determined by the Lowry method (using a kit from Pierce). Samples containing 10–15 µg of protein were loaded onto a 8–16% Tris/glycine gradient polyacrylamide gel electrophoresis PAGE (Novex R and D systems) in Tris/glycine buffer and run for 90 minutes at 125 constant volts, 36 mA. The gel was fixed in 10% glacial acetic acid for 1 hour and samples were blotted onto nitrocellulose membrane. The membranes were incubated in 1% BSA for 1 hour, followed by incubation with GRP1 antiserum (with and without preabsorption) for 1 hour. Antibody binding were detected by the avidin:biotin-peroxidase complex method using diamino-bezidene as the substrate. The Western blot analysis results using Rabbit-antiserum raised against Peptide 1 (Rabbit anti-GRP1 antiserum) are shown in FIG. 7 and FIG. 8.

Figure 7:
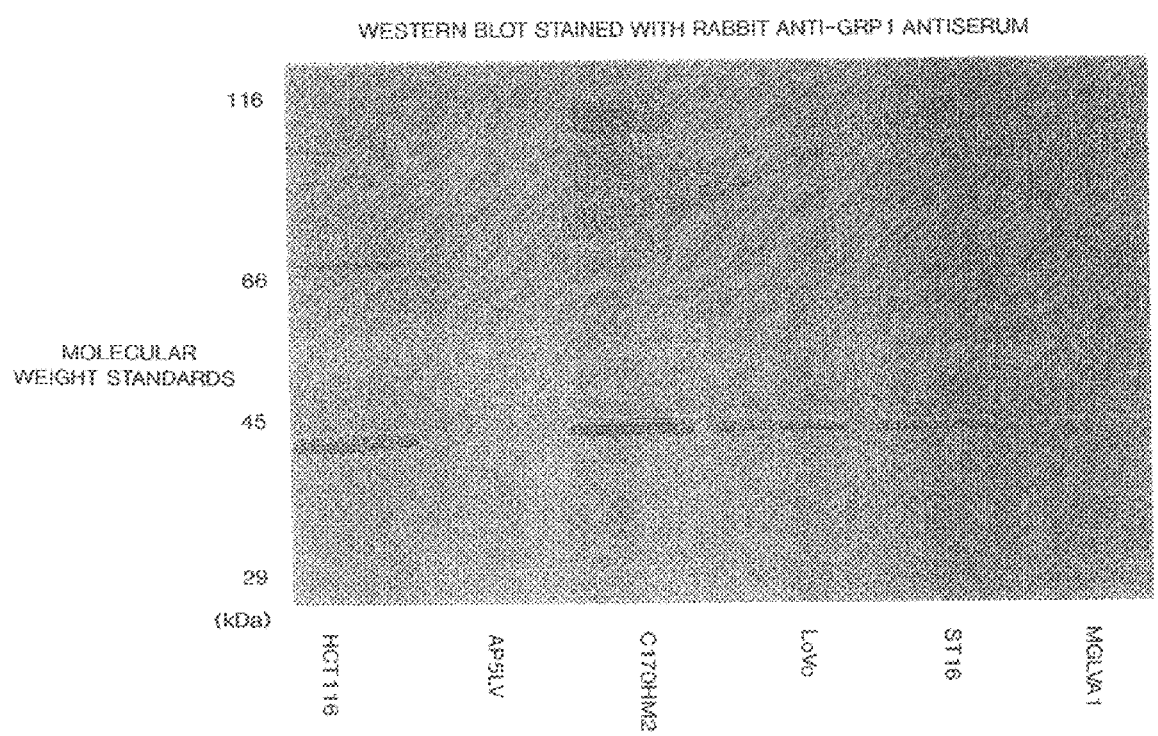
FIG. 7 is a photograph of a Western blot analysis of protein extracts from nuclear membranes of adenocarcinoma cells using antibodies raised against Peptide 1.

As shown in FIG. 7, the protein molecular weight; markers range from 116, 66, 45 and 29 kDa. The blot shows a prominent anti-Peptide 1 immunoreactive band localizing at about 43 kDa in all adenocarcinoma cells studied, i.e., HCT116, C170HM2, LoVo, ST16 and MGLVA1, except one (AP5LV). This protein corresponds to a truncated form of the CCK-B/gastrin-receptor. Some cell lines (HCT 116 and C170HM2) show at least 3 other bands, ranging in molecular weight between 60 and 100 KDa. The data indicate that the anti-CCK-B/gastrin-receptor antibodies can recognize and bind to various isoforms of the CCK-B/gastrin-receptor in tumor cells.

Figure 8:
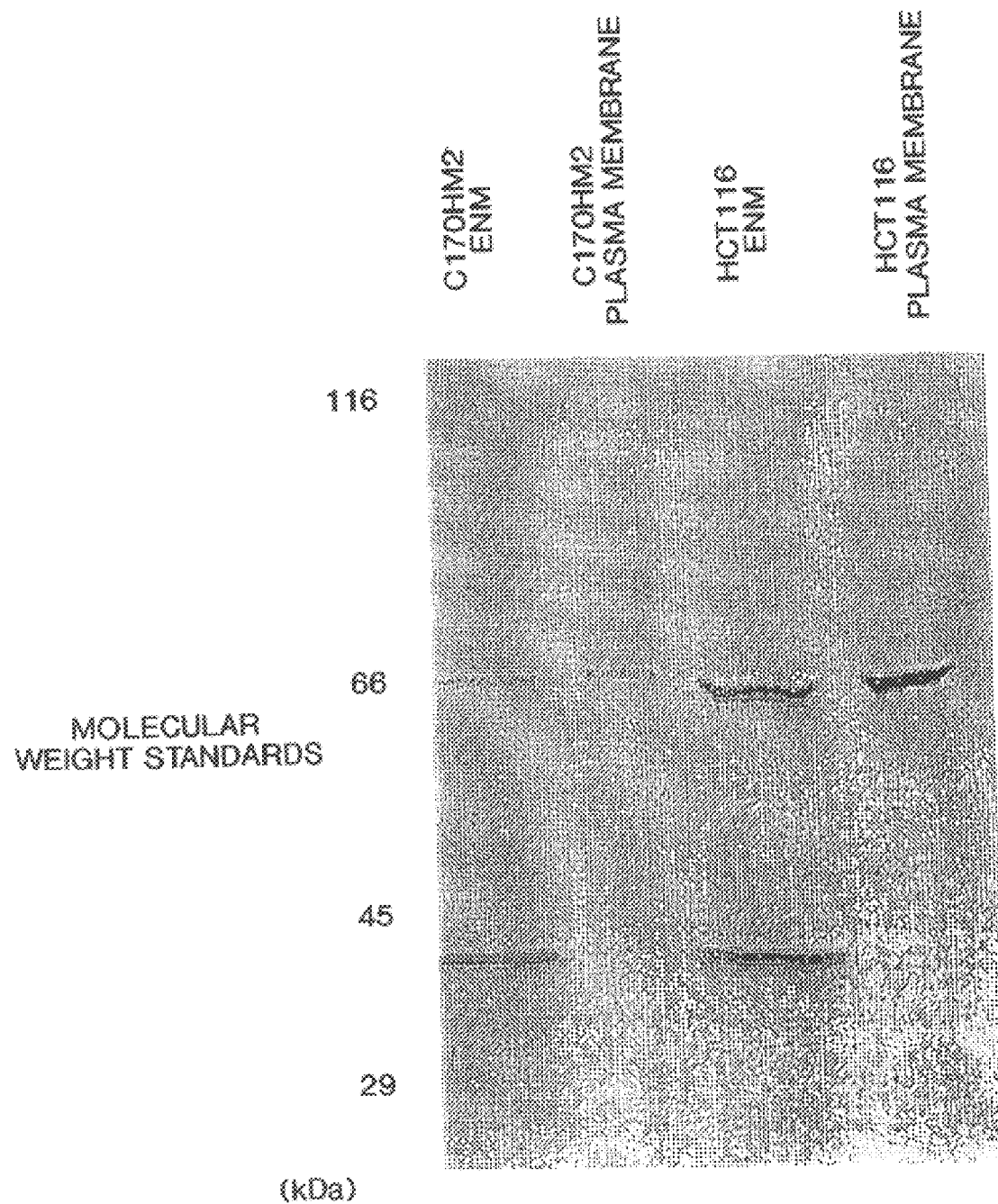
FIG. 8 is a photograph of a Western blot analysis of protein extracts from extranuclear and plasma membranes of adenocarcinoma cells using antibodies raised against Peptide 1.

FIG. 8 shows a Western blot from extranuclear (ENM) and plasma membrane of C170HM2 and HCT116 adenocarcinoma cells. As shown in FIG. 8, adenocarcinoma cell lines tested for ENM CCK-B/gastrin-receptors demonstrate the existence of two strongly stained bands: one about 43 KDa and the other at about 66 KDa. When only the plasma membrane fraction was stained, a single band at about 66 KDa was present. Thus, the Western blot studies confirm the inmuunoEM results that the CCK-B/gastrin-receptor is present in adenocarcinoma tumor cells, although the immunoEM studies do not distinguish between the isoforms of the CCK-B/gastrin-receptor. The data indicate that the present immunogens elicit anti-CCK-B/gastrin-receptor antibodies which can recognize and bind various isoforms of the receptor, which would be advantageous for the treatment of these tumors.

EXAMPLE 7

C170HM2 adenocarcinoma cells were injected intraperitoneally into nude mice and tumors were allowed to grow in the liver. Control mice received an infusion of phosphate buffer saline solution (PBS) and experimental mice received an infusion of one anti-CCK-B/gastrin-receptor antibodies. In Group 1, each mouse was infused daily with 0.5 mg of Rabbit anti-CCK-B/gastrin-receptor antibodies generated against Peptide 1 (Rabbit anti-Peptide 1, Rbt@GRP1). In Group 2, each mouse received daily 0.5 mg of Rabbit anti-CCK-B/gastrin-receptor antibodies generated against Peptide 4 (Rabbit anti-Peptide 4, Rbt@GRP4). The mice were studied for a period of 40 days after antibody infusion, sacrificed and the tumors removed for study. The weight, size and cross-sectional area of the tumors were assessed by standard techniques. The results are shown in FIGS. 9 and 10.

Figure 9:
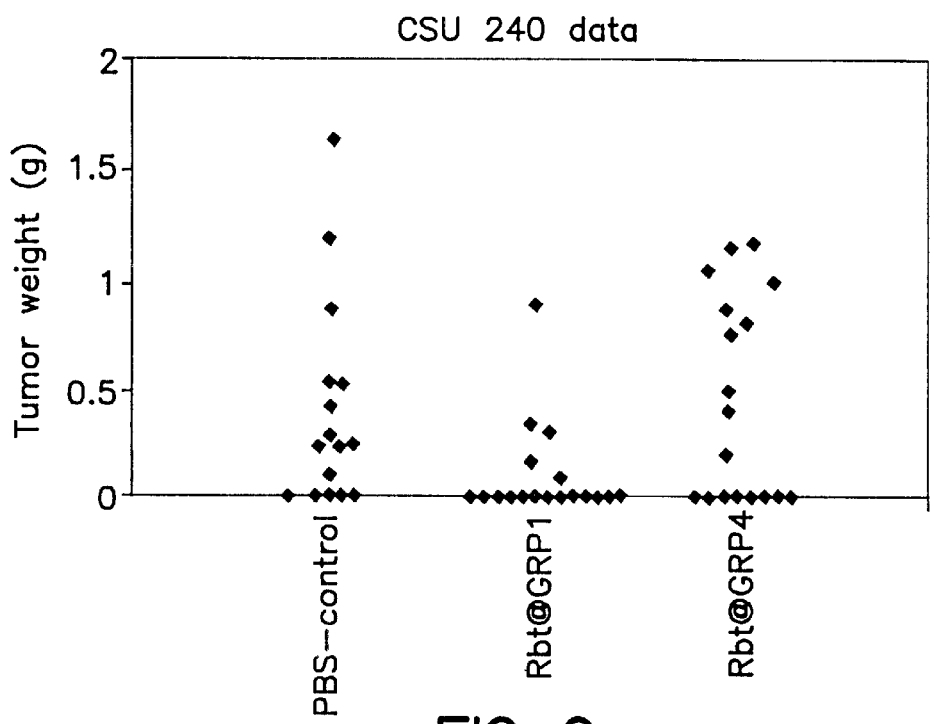
FIG. 9 is a plot graph illustrating the C170HM2 tumor weight of control and anti-CCK-B/gastrin receptor-treated animals.
Figure 10:
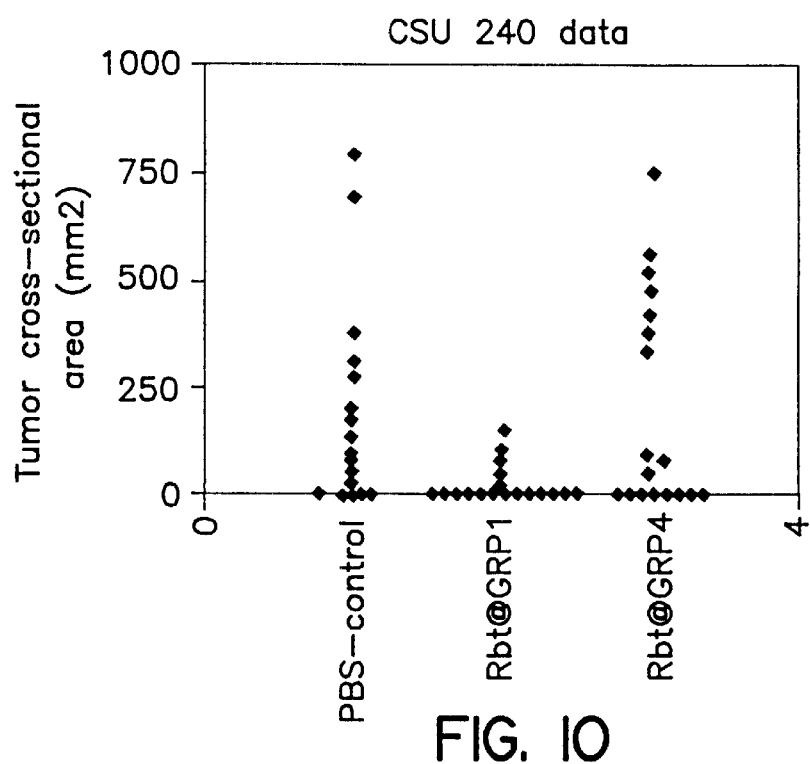
FIG. 10 is a plot graph illustrating the cross-sectional area of C170HM2 tumors from control and anti-CCK-B/gastrin receptor-treated animals.
Figure 11:
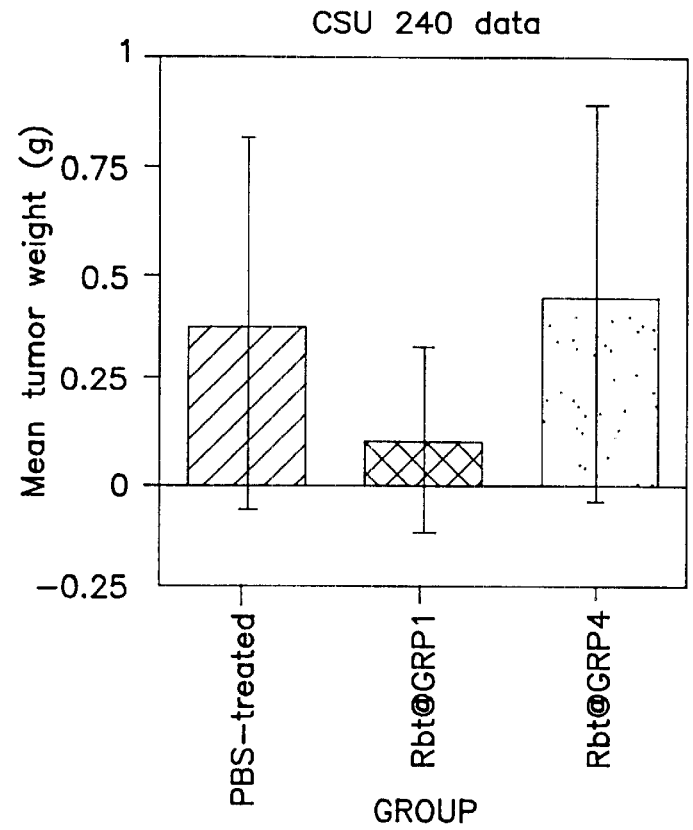
FIG. 11 is a bar graph showing the mean C170HM2 tumor weights of control and anti-CCK-B/gastrin receptor-treated animals.
Figure 12:
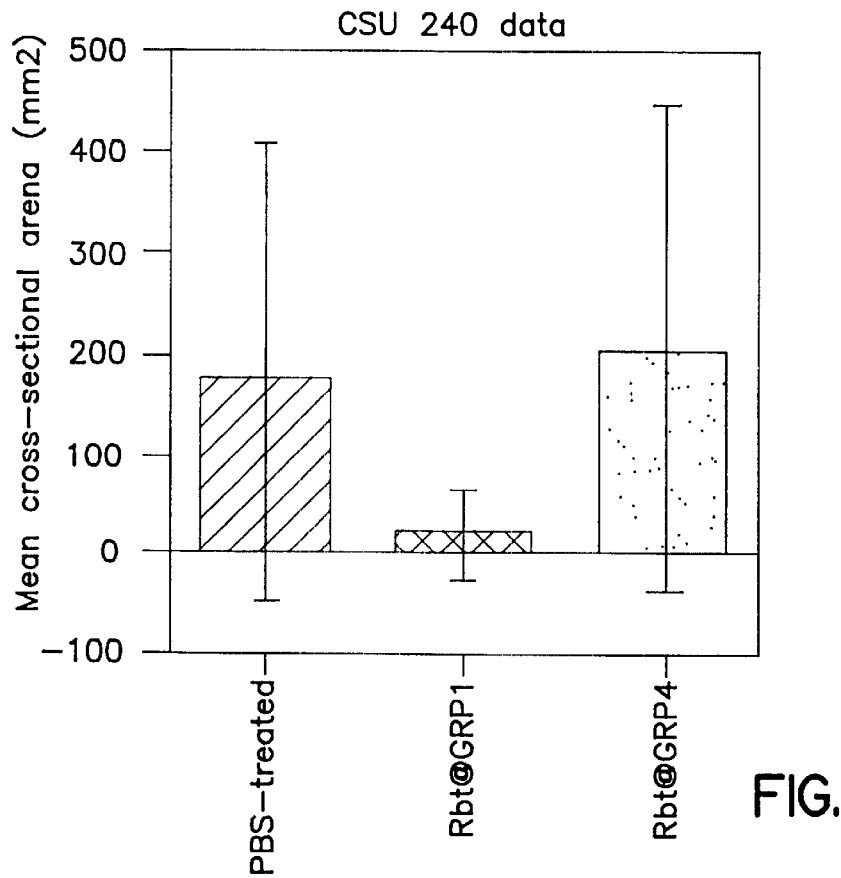
FIG. 12 is a bar graph showing the mean cross-sectional area of C170HM2 tumors of control and anti-CCK-B/gastrin receptor-treated animals.
Figure 13:
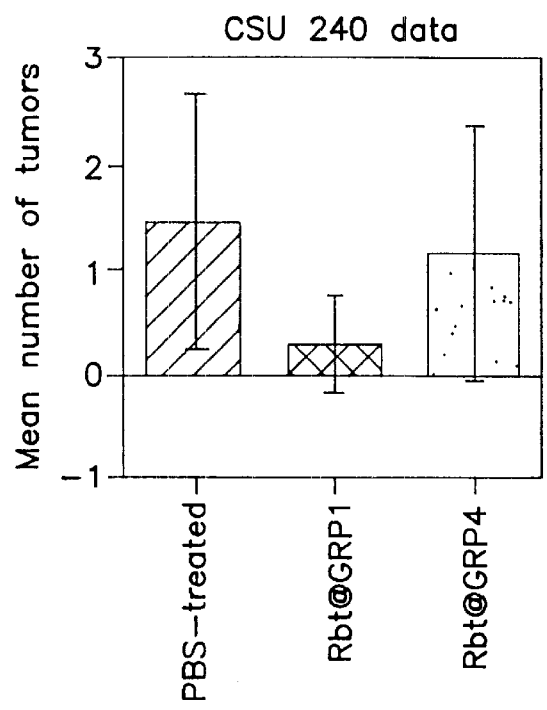
FIG. 13 is a bar graph showing the mean number of C170HM2 tumors in control and anti-CCK-B/gastrin receptor-treated animals.

As seen in FIGS. 9 and 10, implantation of the colorectal adenocarcinoma cancer cell line C170HM2 in mice without treatment results in the rapid growth of large tumor masses, as determined by tumor weight, or tumor size, and the tumor cross-sectional area of the tumors. However, infusion of the animals with Rabbit anti-Peptide 1 or Rabbit anti-Peptide 4 antibodies results in a marked decrease in the number of animals having any detectable tumor, as well as in the weight and size of tumors in animals having them when compared to control. The same effect can be seen when mean tumor weight, mean tumor size, or mean tumor number is calculated. These data are shown in FIGS. 11, 12 and 13.

Figure 14:
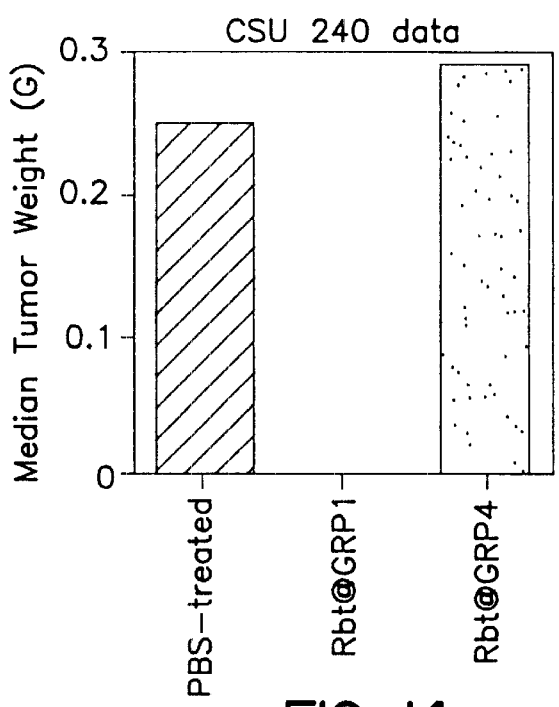
FIG. 14 is a bar graph showing the median C170HM2 tumor weight of liver metastases, of control and anti-CCK-B/gastrin receptor-treated animals.
Figure 15:
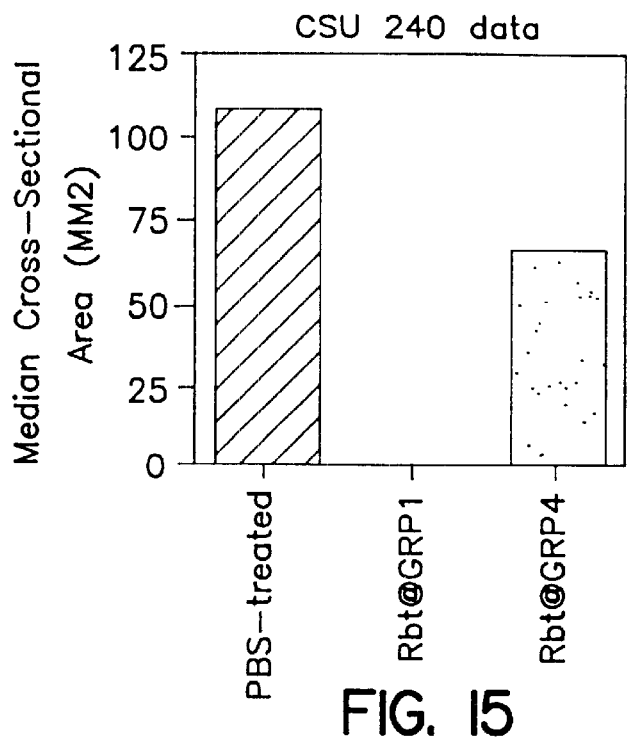
FIG. 15 is a bar graph showing the median cross-sectional area of C170HM2 tumors from control and anti-CCK-B/gastrin receptor-treated animals.
Figure 16:
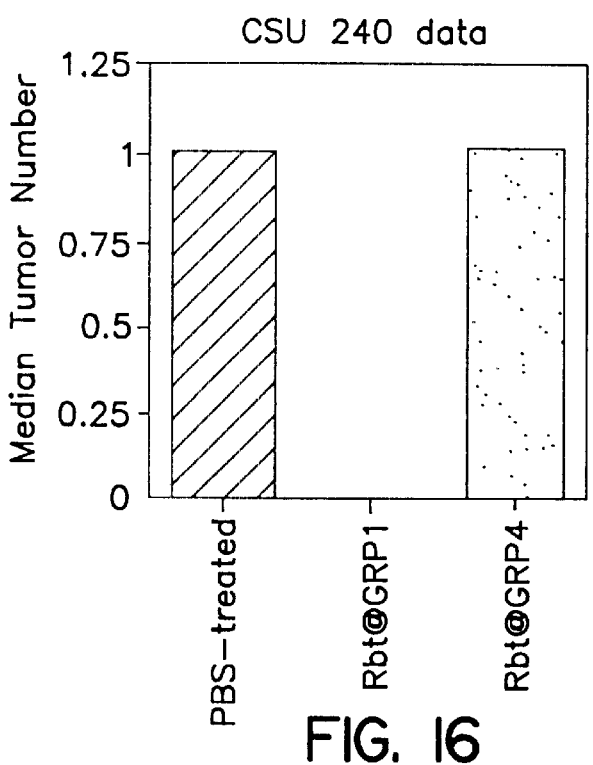
FIG. 16 is a bar graph showing the median C170HM2 tumor number in control and anti-CCK-B/gastrin receptor-treated animals.

Further insight into the distribution within the population is gained by calculating the medians of tumor numbers, weight and size. The results are shown in FIGS. 14, 15 and 16. As seen in these figures, the Rabbit anti-Peptide 1 immunogen was consistently more effective than Rabbit anti-Peptide 4 in inhibiting tumor growth. However, both Rabbit anti-Peptide 1 and Rabbit anti-Peptide 4 antibodies did exhibit powerful tumor inhibitory activity as compared to the control treatment.

EXAMPLE 8

A larger tumor burden was generated in nude mice using the colon cancer cell line C170HM2 by a method as described in Example 7, but with a higher initial cell innoculum. The C170HM2 is a liver-invasive xenograft model. Control and experimental mice were treated also as described in Example 7.

Figure 17:
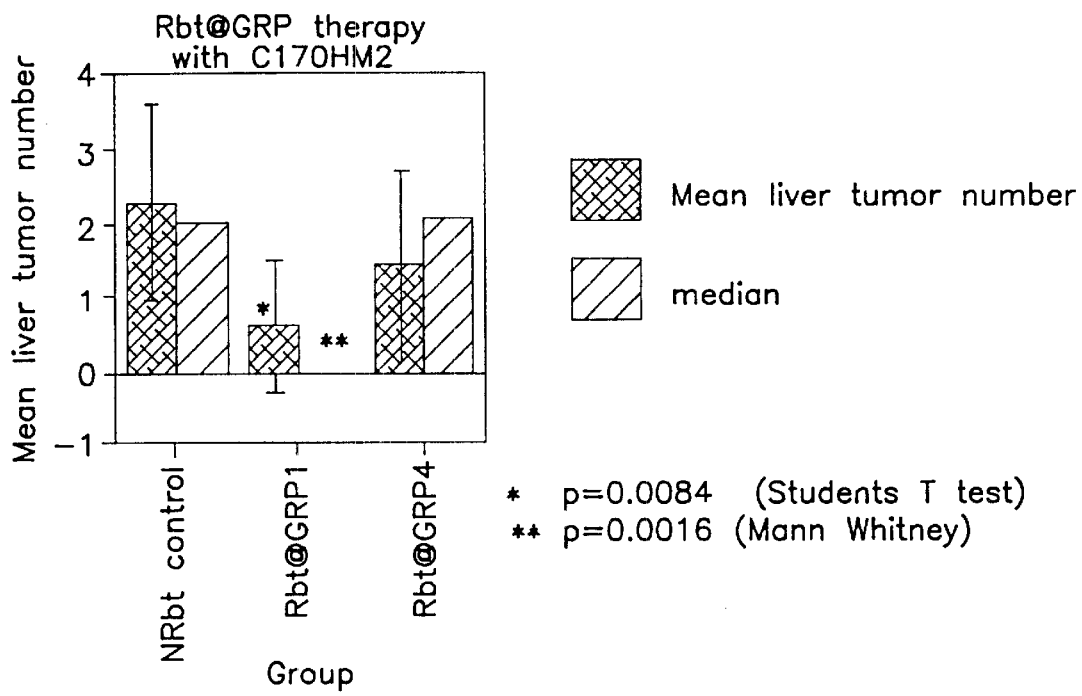
FIG. 17 is a bar graph showing the mean and median liver C170HM2 tumor number in control and anti-CCK-B/gastrin-receptor-treated animals.
Figure 18:
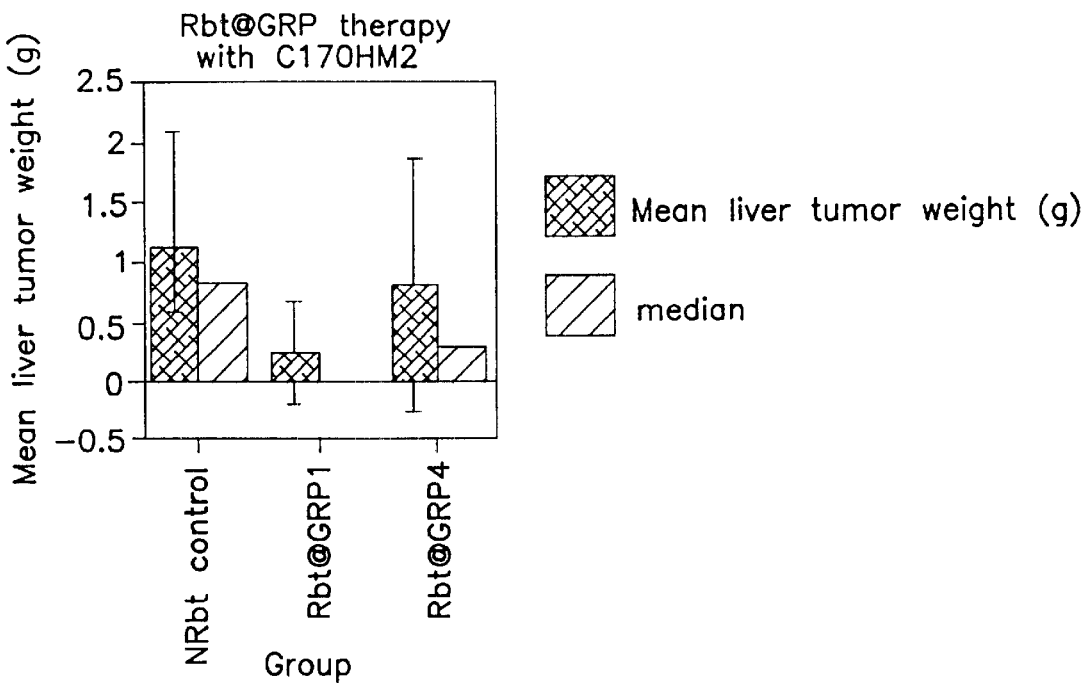
FIG. 18 is a bar graph showing the mean and median liver C170HM2 tumor weight in control and anti-CCK-B/gastrin-receptor-treated animals.
Figure 19:
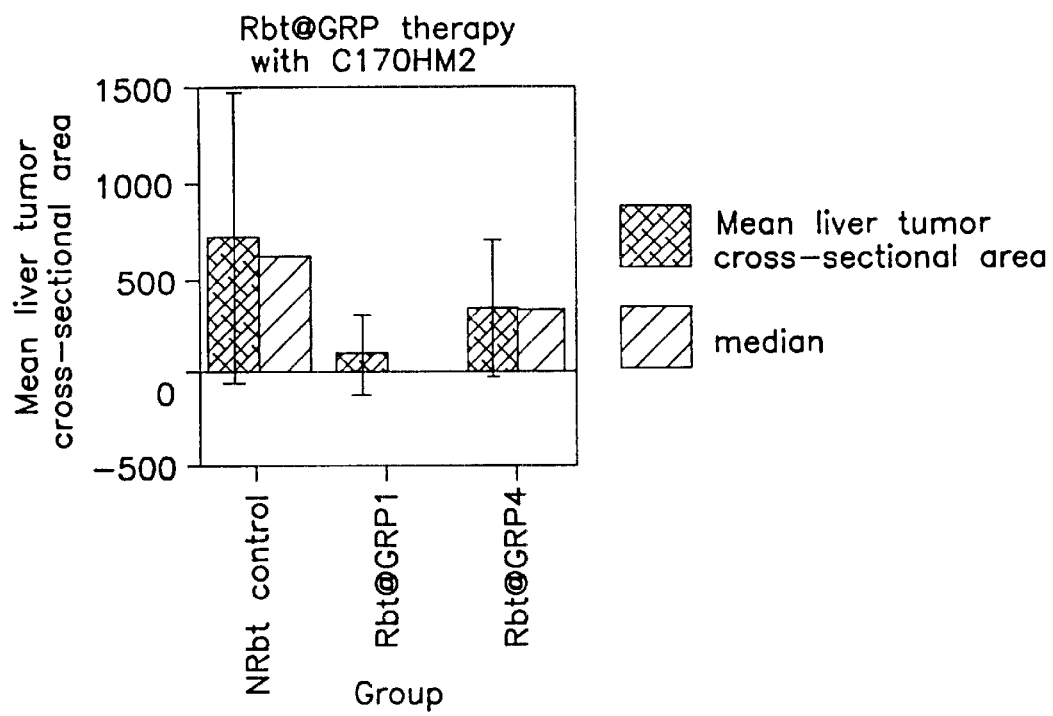
FIG. 19 is a bar graph showing the mean and median values for the cross-sectional area of C170HM2 liver tumor metastases in control and anti-CCK-B/gastrin-receptor-treated animals.

Forty days after antibody infusion, the mice were sacrificed and liver tumors were removed and studied. FIGS. 17, 18 and 19 show the results of these experiments. FIG. 17 shows the mean and median liver tumor numbers of control and anti-CCK-B/gastrin-receptor antibody treated animals. The data show that the Rabbit-anti-CCK-B/gastrin-receptor antibodies ("Rabbit@GRP") are effective in inhibiting the growth of the metastatic tumors in the liver. There is a statistically significant decrease in mean liver tumor numbers in mice livers using Rabbit anti-Peptide 1 (Student's T test), p=0.0084 and in the median liver tumor number, p=0.0016 (Mann Whitney) when compared to controls. Mice treated with anti-Peptide 4 antibodies also show a decrease in mean liver tumor number; however, there was no difference in the mean liver tumor number in this animals when compared to controls.

FIG. 18 shows that anti-Peptide 1 and anti-Peptide 4 antibodies were also capable of reducing the mean and median tumor weights of liver metastases when compared to control animals. The data in FIG. 19 show that anti-CCK-B/gastrin-receptor treated mice also had a significant decrease in mean and median cross-sectional area of the liver tumors when compared to control animals.

The data indicate that the anti-CCK-B/gastrin-receptor antibodies are effective in controlling the spread and growth of a gastrin-dependent colon cancer in the liver, which constitutes the major site of metastatic spread of this cancer.

EXAMPLE 9

These studies we carried out to confirm GRP1 immunoreactivity on C170HM2 cells. The aim of the study was to evaluate tumor localization of antiserum raised against GRP1 and to determine its therapeutic effect on the growth of C170HM2 cells within the liver of nude mice. C170HM2 cells were injected intraperitoneally into nude mice as described in Examples 7 above. GRP1 antiserum was raised in rabbits. The antiserum was radiolabelled with $^{125}$I and administered to nude mice with established C170HM2 xenografts by a tail vein injection. Control mice received $^{125}$I radiolabelled normal rabbit serum. Mice were terminated at increasing time points following injection of a single dose of $^{125}$I antibodies. Radioactivity was measured as counts per minute per gram of (CPM/g) tissue and the liver/liver tumor ratio calculated.

Figure 20:
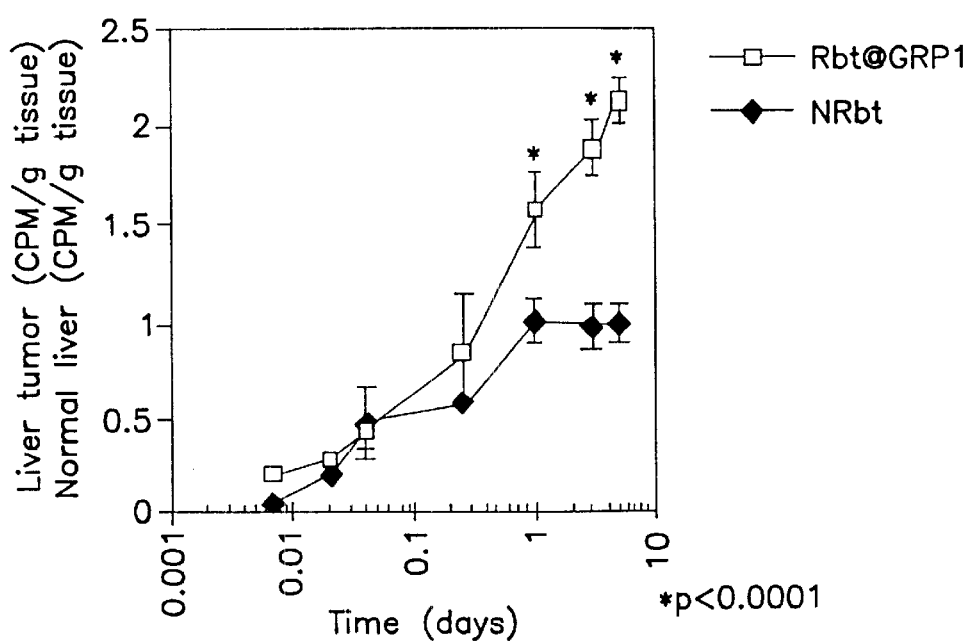
FIG. 20 depicts a graph showing the concentration of radiolabeled $^{125}$I-antibodies in C170HM2 liver tumor xenografts of control (normal rabbit serum) and anti-GRP1-treated nude mice.

FIG. 20 is a graph which shows the radiolabeled rabbit anti-GRP1 antibodies bound to liver tumors versus control. As seen in the figure, more rabbit anti-GRP1 antibodies are bound to liver tumor tissue when compared to controls. FIG. 20 also shows the liver tumor/liver ratio on the y axis with increasing time on the x axis for both radiolabeled normal rabbit serum and GRP1 antiserum. The normal rabbit serum achieved a ratio of 1 from day 1 which remained constant until day 5. This indicates the level of radiolabel in the liver tumour and normal liver was equal. The ratio for GRP1 antiserum accumulated exponentially approaching 2 by day 5. This indicates radiolabeled GRP1 antiserum specifically localizes within C170HM2 liver tumors.

EXAMPLE 10
Therapeutic Effect of GRP1 Antiserum on C170HM2 Xenografts

The C170HM2 tumor xenografts were initiated by intraperitoneal injections of cells. Three different cell inocula were used to generate 3 levels of tumor burden. The GRP1 antiserum was administered passively by tail vein injection daily from day 0. Therapy was terminated on day 40.
Effect of GRP1 Antiserum on Tumor 'Take Rate'

Figure 21:
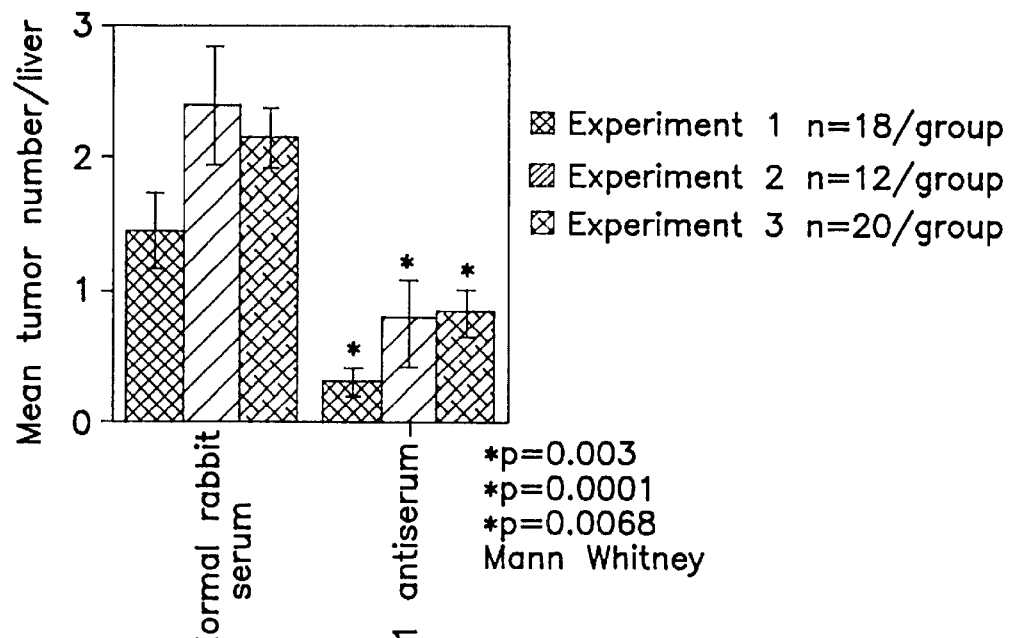
FIG. 21 depicts a bar graph showing the mean C170HM2 liver tumor number per liver of xenografts of control and anti-GRP1-treated nude mice.
Figure 22:
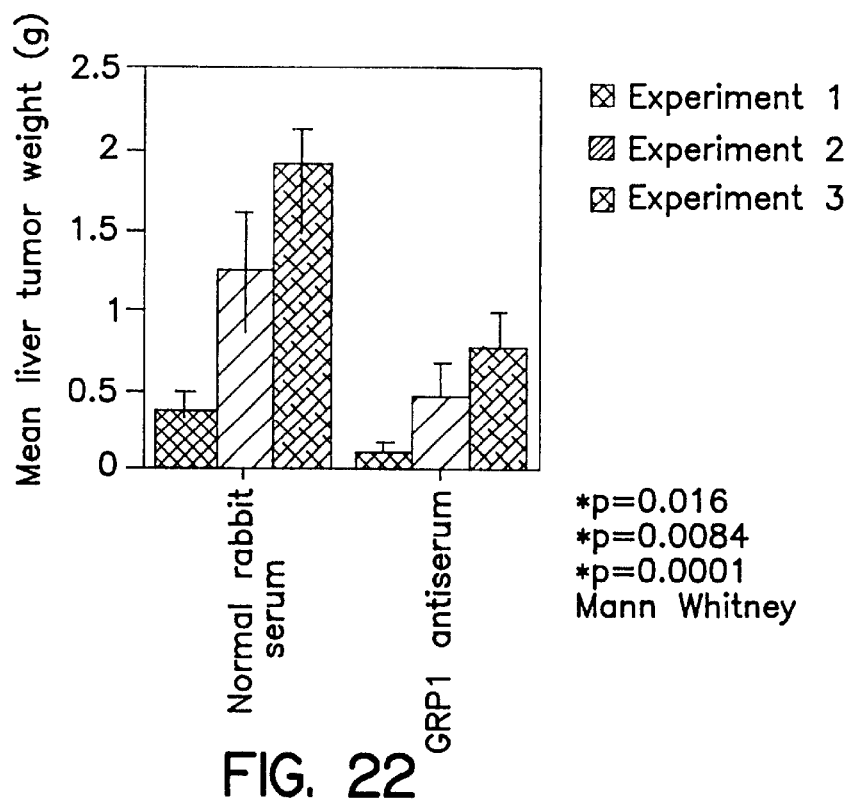
FIG. 22 depicts a bar graph showing the mean C170HM2 liver tumor weight of liver xenografts of control and anti-GRP1-treated nude mice.
Figure 24:
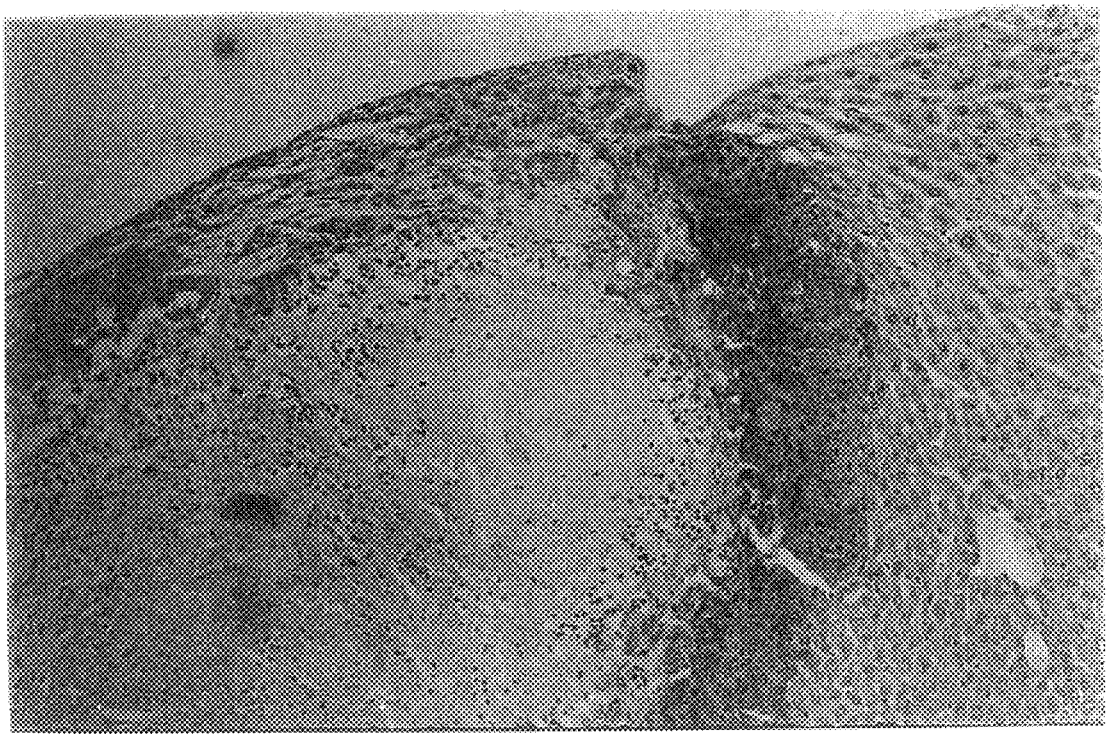
FIG. 24 is a photograph of a histological section taken with a light microscope showing a hematoxylin/eosin-stained section of a C170HM2 liver xenograft of a control mouse.
Figure 25:
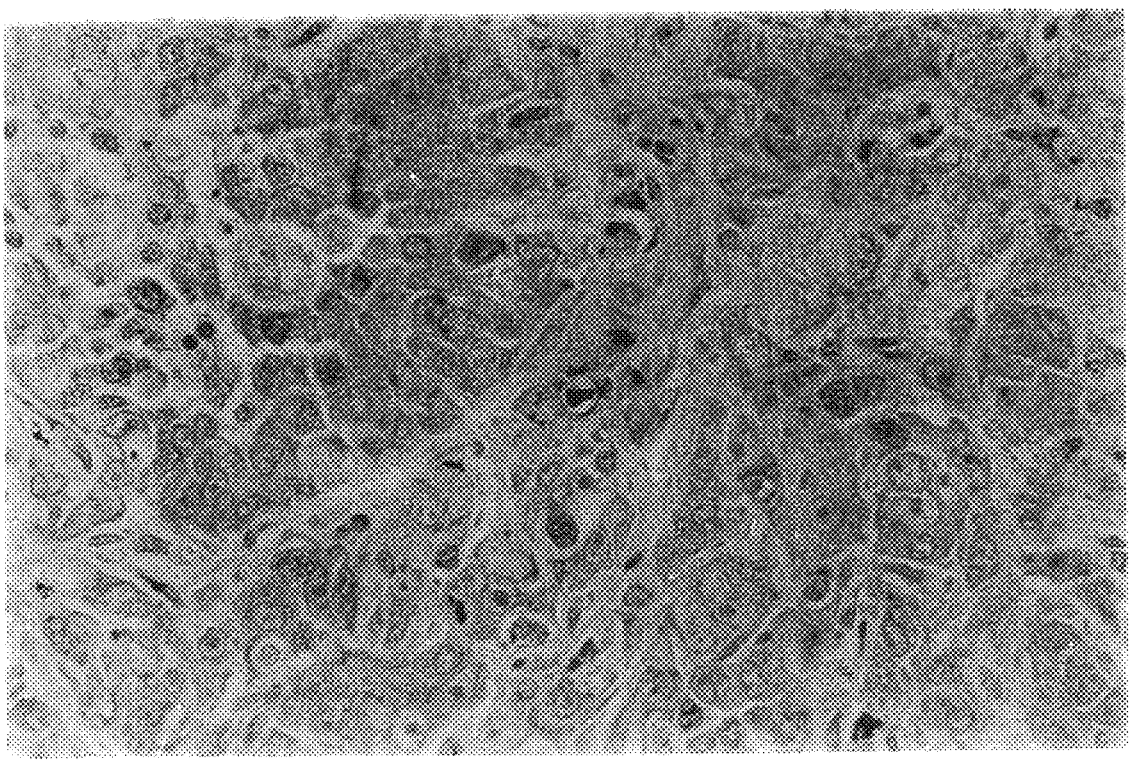
FIG. 25 is a photograph of a histological section taken with a flight microscope showing a hematoxylin/eosin stained section of a C170HM2 liver xenograft from a mouse treated with rabbit anti-GRP1 antibodies.

The initial parameter evaluated was mean tumor number within the liver which is shown in FIG. 21. The normal rabbit antiserum treated controls are grouped in increasing cell inocula. As seen in FIG. 21, in the control groups the mean tumor number per liver was between 1 and 3. In the GRP1 antiserum treated group the mean tumor number per liver was less than 1 for all three cell inocula, which was significant for all 3 experiments (one inoculum, n=18, p=0.003; 2 inocula, n=12, p=0.0001 and 3 inocula, n=20, p=0.0068, Mann Whitney analysis).
Effect of GRP1 Antiserum on Tumor Weight of Established Tumors FIG. 22 shows the mean tumor weight for the normal rabbit serum treated controls on the left panel for the 3 increasing cell innocula. The figure also shows the mean tumor weight of nude mice following treatment with GRP1 antiserum the mean liver weight was reduced by 60% with all 3 cell innocula, which was significant for all 3 experiments (one inoculum, p=0.0016; 2 innocula, p=0.0084, and 3 innocula, p=0.0001, Mann Whitney analysis).
GRP1 Immunoreactivity in C170HM2 Xenografts as Determined by Western Blotting Extra-nuclear membrane proteins were prepared from C170HM2 xenografts from 2/3 experiments. These were analyzed by Western blotting using the GRP1 antiserum. FIG. 23 is a photograph of the Western blot showing in the normal rabbit serum-treated xenografts 2 immuno-reactive bands were present at 74 and 50 kDa, with the former band showing the strongest immunoreactivity. In the GRP1 antiserum treated xenografts, there are 2 immuno-reactive bands together with an intermediate band, not seen in the control xenografts or cells grown in vitro. A 50 kDa band shows the strongest immunoreactivity. This indicates that in the GRP1 antiserum treated xenografts a larger proportion of the CCKB/gastrin-receptors may be present as an internalized form.
Histological Analysis of C170HM2 Xenografts FIG. 24 shows a microscopic view of a C170HM2. xenograft invading a liver of a nude mouse. The tumor is generally composed of a necrotic center with a viable leading edge which squashes the hepatocytes as it invades the liver. The degree of apoptosis was measured in the viable leading edge of C170HM2 tumors by the Tunel method with positive cells visualized by in situ hybridization. FIG. 25 shows that apoptotic cells were present in the viable tumor cells in the GRP1 antiserum-treated xenografts, but not in the normal rabbit serum-treated tumors.

The data show that antiserum raised against the amino terminal epitope of the CCKB/gastrin-receptor selectively localizes within liver-invasive C170HM2 tumors. Neutralization of the GRP1 epitope induced a significant effect on both tumor 'take rate' and gross tumor burden of tumors that did establish. This tumor-inhibitory effect may be due to (a) a general cytostatic effect induced by blocking the CCKB/gastrin-receptor and/or (b) an indirect effect of targeting an antibody to the nucleus of the cell, possibly resulting in apoptosis.

REFERENCES

1. Bock, M. G., DiPardio, R. M., Evans, B. E., Rittle, K. E., Whitter, A., Veber, D, Anderson, E., and Freidinger, A. Benzodiazepine, gastrin and brain cholecystokinin receptor ligands: L-365,260. J. Med. Chem., 32: 13–17, 1989.
2. Curtis, B. M., Widmer, M. B., de Roos, P., Qwarnstrom, E. E. IL-1 and its receptor are translocated to the nucleus. J. Immunol. 1990; 144:1295–1303.
3. Dickinson C. J. Relationship of gastrin processing to colon cancer (editorial). Gastroenterology 1995; 109:1384–1388.
4. Edkins, J. S. On the chemical mechanism of gastric secretion. Proc. Soc. Lond. 1905; 76:376.
5. Fourmy, D., Zahidi, A., Pradayrol, I., Vay ssette, J., Ribet, A. Relationship of CCK/gastrin-receptor binding to amylase release in dog pancreatic acini. Regul. Pept. 1984; 10:57–68.
6. Grider, J. R., Malchlouf, G. M. Distinct receptors for cholecystokinin and gastrin on muscle cells of stomach and gallbladder. Am. J. Physiol. 1990; 259:G184-G190.
7. Harrison's Principles of Internal Medicine, Isselbacher et al. Eds. 13$^{th}$ Ed. Pages 1690–1691, 1994.
8. Holt, S. J., Alexander, P., Inman, C., Davies, D. Epidermal growth factor induced tyrosine phosphorylating of nuclear proteins associated with translocation of epidermal growth factor receptor into the nucleus. Biochem. Pharm. 1994; 43:117–126.
9. Hughes, J., Boden, P., Costall, B., Domeney, A., Kelly, E., Horwell, D. C., Hunter, J. C., Pinnock, R. D., and Woodruff, G. N. Development of a class of selective cholecystokinin type B receptor antagonists having potent anxiolytic activity. Proc. Natl. Acad. Sci., 87: 6728–6732, 1990.
10. Johnson L. New aspects of the trophic actin of gastrointestinal hormones. Gastroenterology 1997; 72:788–792.
11. Kopin, A. S., Lee, Y. M., McBride, E. W., Miller, L. J., Lu, M., Lin, H. Y., Kolakowski, L. F., Beinborn, M. Expression cloning and characterization of the canine parietal cell gastrin-receptor. Proc. Nat. Acad. Sci. USA 1992; 89:3605–3609.

12. Laudron P. M. From receptor internalization to nuclear translocation: new targets for long-term pharmacology. Biochem. Pharm. 1994; 47:3–13.
13. Le Meuth, V., Philouz-Rome, V., LeHuerou-Luron, L., Formal, M., Vaysse, N., Gespach, C., Guilloteau, P., Fourmy, D. Differntial expression of A- and B-subtypes of cholecystokinin/gastrin-receptors in the developing calf pancreas. Endocrinology 1993; 133:1182–1191.
14. Matsumoto, M., Park, J., Yamada, T. Gastrin-receptor characterization: affinity cross-linking of the gastrin-receptor on canine gastric parietal cells. Am. J. Physiol. 1987; 252:G143–147.
15. Nakata, H., Matsui, T., Ito, M., Taniguchi, T., Naribayashi, Y., Arima, N., Nakamura, A., Kinoshita, Y., Chibara, K., Hosoda, S., Chiba, T. Cloning and characterization of gastrin-receptor from ECL carcinoid tumor of Mastomys natalensis. Biochem. Biophys. Res. Commun. 1992; 187:1151–1157.
16. Narayan, S., Chicone, L., Singh, P. Characterization of gastrin binding to colonic mucosal membranes of guinea pigs. Mol. Cell. Biochem. 1992; 112:163–171.
17. Palnaes, Hansen C., Stadil, F., Rehfeld, J. F. Metabolism and influence of glycine-extended gastrin on gastric acid secretion in man. Digestion 1996; 57:22–29.
18. Podlecki, D. A., Smith. R. M., Kao, M., Tsai, P., Huecksteadt, T., Brandenburg, D., Lasher, R. S., Jarett, L., Olefsky, J. M. Nuclear translocation of the insulin receptor. J. Biol. Chem. 1987; 262:3362–3368.
19. Rehfeld, J. F., Bardram, L., Hilsted, L. Gastrin in human bronchogenic carcinomas, constant expression but variable processing of prograstrin. Cancer Res. 1989; 49:2840–2843.
20. Romani, R., Howes, L. G., and Morris, D. L. Potent new family of gastrin-receptor antagonists (GRAs) produces in vitro and in vivd inhibition of human colorectal cancer cell lines. Procs. AACR, 35: 397 (Abstract), 1994.
21. Scemma, J. L., Fourmy, A., Zahidi, L., Praydayrol, L., Susini, C., Ribet, A. Characterization of gastrin-receptors on a rat pancreatic acinar cell line (AR4-2J). A possible model for studying gastrin mediated cell growth and proliferation. Gut 1987; 28:233–236.
22. Seva, C., Dickinson, C. J., Yamada, T. Growth-promoting effects of glycine-extended prograstrin. Science 1994; 265:410–412.
23. Singh, P., Owlia, A., Espeijo, R., Dai, B. Novel gastrin-receptors mediate mitogenic effects of gastrin and processing intermediates of gastrin on Swiss 3T3 fibroblasts. Absence of detectable cholecystokinin (CCK)-A and CCK-B receptors. J. Biol. Chem. 1995; 270:8429–8438.
24. Singh, P., Townsend, Jr. C. M., Thompson, J. C., Narayan, S., Guo, Y. S. Hormones in colon cancer: past and prospective studies. Cancer J. 1990; 3:28–33.
25. Soll, A. H., Amiran, L. P., Thomas, T., Reedy, T. J., Elashoff, J. D. Gastrin-receptors on isolated canine parietal cells. J. Clin. Invet. 1984; 73:1434–1447.
26. Taniguchi, T., Matsui, T., Ito, M., Marayama, T., Tsukamota, T., Katakami, Y., Chiba, T., Chihara, K. Cholecystokinin-B/gastrin-receptor signaling pathway involve styrosine phosphorylatins of p125FAK and p42MAP. Oncogene 1994; 9:861–867.
27. Todisco, A., Takeuchi, Y., Seva, C., Dickinson, C. J., Yamada, T. Gastrin and glycine-extended prograstrin processing intermediates induce different programs of carly gene activation. J. Biol. Chem. 1995; 279:28337–28341.
28. Ulrich, A., Schlessinger, J. Signal transduction by receptors with tyrosine kinase activity. Cell 1990; 61:203–212.
29. Wank, S. A. Cholecystokinin receptors (editorial). Am. J. Physiol. 1995; 269:G628–G646.
30. Wank, S. A., Pisegna, J. R., de Weerth, A. Brain and gastrointestinal cholecystokinin receptor family: structure and functional expression. Proc. Nat. Acad. Sci. USA 1992; 89:8691–8695.
31. Watson, S. A., Durrant, L. G., Crosbie, J. D, Morris D. L. The in vitro growth response of primary human colorectal and gastric cancer cells to gastrin. Int. J. Cancer 1989; 43:692–696.
32. Watson, S. A., Durrant, L. G., Elston, P., and Morris, D. L. Inhibitory effects of the gastrin-receptor antagonist (L-365,260) on gastrointestinal tumor cells. Cancer,
33. Watson, S. A., Steele, R. Gastrin-receptors on gastrointestinal tumor cells, In: Gastrin-receptors in Gastrointestinal Tumors. R. G. Landes Co.; Austin Tex.:CRC 1993 p. 20–

We claim:

1. An immunogen comprising: a human CCK-B/gastrin receptor-immunomimic peptide consisting of the amino acid sequence KLNRSVQGTGPGPGASL (SEQ ID NO: 1) or GPGAHRALSGAPISF (SEQ ID NO: 2) linked at one of its ends to a spacer peptide conjugated to an immunogenic carrier.

2. An immunogen comprising: a human CCK-B/gastin receptor-immunomimic peptide consisting of the amino acid sequence KLNRSVOGTGPGPGASL (SEQ ID NO: 1) conjugated to an immunogenic carrier.

3. An immunogen comprising: a human CCK-B/gastrin receptor-immunomimic peptide consisting of the amino acid sequence GPGAHRALSGAPISF (SEQ ID NO: 2) linked at one of its ends to a spacer peptide conjugated to an immunogenic carrier.

4. The immunogen of claim 1 or 3 wherein the spacer peptide is SSPPPPC (SEQ ID NO: 3).

5. The immunogen as claimed in anyone of the claims 1–3 wherein the immunogenic carrier is selected from the group consisting of Diphtheria toxoid, tetanus toxoid, and bovine serum albumin.

6. An immunogenic composition comprising an inmunogen as claimed in anyone of the claims 1–3.

7. An immunogenic composition comprising an anti-human CCK-B/gastrin receptor immunogen comprising:
    a receptor-immunomimic peptide consisting of the amino acid sequence KLNRSVQGTGPGPGASL (SEQ ID NO: 1) which is linked at its carboxyterminal end to a spacer peptide consisting of the amino acid sequence SSPPPPC (SEQ ID NO: 3) conjugated to an immunogenic carrier.

8. The composition as claimed in claim 6 or 7, wherein the human CCK-B/gastrin receptor is expressed by gastrin-dependent tumors.

9. An immunogenic composition comprising an anti-human CCK-B/gastrin receptor immunogen comprising:
    a receptor-immunomimic peptide consisting of the amino acid sequence GPGAHRALSGAPISF (SEQ ID NO: 2) which is linked at its carboxy-terminal end to a spacer peptide consisting of the amino acid sequence SSPP-PPC (SEQ ID NO: 3) conjugated to an immunogenic carrier.

* * * * *

SEQUENCE LISTING

```
(1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 17 amino acids
        (B) TYPE: amino acid
        (C) STRANDEDNESS: Not Relevant
        (D) TOPOLOGY: linear (ii) MOLECULE TYPE: peptide (iii) HYPOTHETICAL: NO (iv) ANTI-SENSE: NO (v) FRAGMENT TYPE: N-terminal
```

```
(xi) SEQUENCE DESCRIPTION: SEQ ID NO:1:

Lys Leu Asn Arg Ser Val Gln Gly Thr Gly Pro Gly Pro Gly Ala Ser
1               5                  10                 15

Leu (2) INFORMATION FOR SEQ ID NO:2:

(i) SEQUENCE CHARACTERISTICS:
         (A) LENGTH: 15 amino acids
         (B) TYPE: amino acid
         (C) STRANDEDNESS: Not Relevant
         (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:2:

Gly Pro Gly Ala His Arg Ala Leu Ser Gly Ala Pro Ile Ser Phe
1               5                  10                 15

(2) INFORMATION FOR SEQ ID NO:3:

(i) SEQUENCE CHARACTERISTICS:
         (A) LENGTH: 7 amino acids
         (B) TYPE: amino acid
         (C) STRANDEDNESS: Not Relevant
         (D) TOPOLOGY: linear (ii) MOLECULE TYPE: peptide (xi) SEQUENCE DESCRIPTION: SEQ ID NO:3:

Ser Ser Pro Pro Pro Pro Cys
1               5
```